US007550561B1

(12) United States Patent
Beach et al.

(10) Patent No.: US 7,550,561 B1
(45) Date of Patent: Jun. 23, 2009

(54) P16$^{INK4}$ POLYPEPTIDES

(75) Inventors: David H. Beach, Huntington Bay, NY (US); Douglas J. Demetrick, E. Northport, NY (US); Manuel Serrano, Mill Neck, NY (US); Gregory J. Hannon, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 0 days.

(21) Appl. No.: 08/227,371

(22) Filed: Apr. 14, 1994

Related U.S. Application Data

(63) Continuation-in-part of application No. 08/154,915, filed on Nov. 18, 1993, now abandoned, which is a continuation-in-part of application No. 07/991,997, filed on Dec. 17, 1992, now abandoned, which is a continuation-in-part of application No. 07/963,308, filed on Oct. 16, 1992, now abandoned, which is a continuation-in-part of application No. 07/888,178, filed on May 26, 1992, now abandoned, which is a continuation-in-part of application No. 07/701,514, filed on May 16, 1991, now abandoned.

(51) Int. Cl.
*C12Q 1/68* (2006.01)
*C12P 21/04* (2006.01)
*C07K 14/435* (2006.01)

(52) U.S. Cl. ................ 530/350; 530/324; 530/352; 530/395; 530/402; 530/403; 435/6; 435/69.1; 435/69.7

(58) Field of Classification Search ............... 530/350, 530/352, 395, 402, 403, 324; 435/6, 69.1, 435/69.7
See application file for complete search history.

(56) References Cited

U.S. PATENT DOCUMENTS 6,110,700 A * 8/2000 Arnold .................. 435/69.1

FOREIGN PATENT DOCUMENTS

| WO | WO 91/16429 | 10/1991 |
|---|---|---|
| WO | WO 92/06180 | 4/1992 |
| WO | WO 92/19749 | 11/1992 |
| WO | WO 92/20316 | 11/1992 |
| WO | WO 92/22635 | 12/1992 |
| WO | WO 93/04701 | 3/1993 |
| WO | WO 93/15227 | 8/1993 |
| WO | WO 94/09135 | 4/1994 |

OTHER PUBLICATIONS

Bates, S. et al. (1993) "CDK6 (PLSTIRE) and CDK4 (PSK-J3) are a distinct subset of the cyclin-dependent kinases that associate with cyclin D1" *Oncogene*, vol. 9, pp. 71-79.

Booher, R.N. et al. (1989) "The Fission Yeast cdc2/cdc13/suc1 Protein Kinase: Regulation of Catalytic Activity and Nuclear Localization" *Cell*, vol. 58, pp. 485-497.

Cannon-Albright, L.A. (1992) "Assignment of a Locus for Familial Melanoma, MLM, to Chromosome 9p13-p22" *Science*, vol. 258, pp. 1148-1152.

Cavenee, W.K. et al. (1983) "Expression of recessive alleles by chromosomal mechanisms in retinoblastoma" *Nature*, vol. 305, pp. 779-784.

Cavenee, W.K. et al. (1986) "Prediction of Familial Predisposition to Retinoblastoma" *The New England Journal of Medicine*, vol. 314, No. 19, pp. 1201-1207.

Cheng, J.Q. et al. (1993) "Homozygous Deletions within 9p21-p22 Identify a Small Critical Region of Chromosomal Loss in Human Malignant Mesotheliomas" *Cancer Research*, vol. 53, pp. 4761-4763.

Coleman, A. et al. (1994) "Distinct Deletions of Chromosome 9p Associated with Melanoma versus Glioma, Lung Cancer and Leukemia" *Cancer Research*, vol. 54, pp. 344-348.

Ewen, M.E. et al. (1993) "Functional Interactions of the Retinoblastoma Protein with Mammalian D-type Cyclins" *Cell*, vol. 73, pp. 487-497.

Fang, F. and Newport, J.W. (1993) "Distinct roles of cdk2 and cdc2 in RP-A phosphorylation during the cell cycle" *Journal of Cell Science*, vol. 106, pp. 983-984.

Fields, S. and Song, O. (1989) "A novel genetic system to detect protein-protein interactions" *Nature*, vol. 340, No. 6230, pp. 245-246.

Friend, S.H. et al. (1987) "Deletions of a DNA sequence in retinoblastomas and mesenchymal tumors: Organization of the sequence and its encoded protein" *Proc. Natl. Acad. Sci. USA*, vol. 84, pp. 9059-9063.

Giordano, A. et al. (1989) "A 60 kd cdc2-Associated Polypeptide Complexes with the E1A Proteins in Adenovirus-Infected Cells" *Cell*, vol. 58, pp. 981-990.

Green, M.R. (1989) "When the Products of Oncogenes and Anti-Oncogenes Meet" *Cell*, vol. 56, pp. 1-3.

Hansen, M.F. and Cavenee, W.K. (1988) "Retinoblastoma and the progression of tumor genetics" *Trends and Genetics*, vol. 4, No. 5, pp. 125-128.

Inaba, T. et al. (1992) "Genomic Organization, Chromosomal Localization, and Independent Expression of Human Cyclin D Genes" *Genomics*, vol. 13, pp. 565-574.

(Continued)

*Primary Examiner*—Ilia Ouspenski
(74) *Attorney, Agent, or Firm*—Wilmer Cutler Pickering Hale and Dorr LLP

(57) ABSTRACT

The present invention relates to the discovery in eukaryotic cells, particularly human cells, a novel polypeptide of 16 kDa (hereinafter "p16$^{INK4}$" or "p16") can function as an inhibitor of cell cycle progression, and therefore ultimately of cell growth, and that similar to the role of p21 and p53, the p16 protein may function coordinately with the cell cycle regulatory protein, retinoblastoma (Rb).

17 Claims, 10 Drawing Sheets

OTHER PUBLICATIONS

Kamb, A. et al. (1994) "A Cell Cycle Regulator Potentially Involved in Genesis of Many Tumor Types" *Science*, vol. 264, pp. 436-440.

Kato, J-Y. et al. (1993) "Direct binding of cyclin D to the retinoblastoma gene product (pRb) and pRb phosphorylation by the cyclin D-dependent kinase CDK4" *Genes & Development*, vol. 7, pp. 331-342.

Knudson, Jr., A.G. (1971) "Mutation and Cancer: Statistical Study of Retinoblastoma" *Proc. Natl. Acad. Sci.* USA, vol. 68, No. 4, pp. 820-823.

Lew, D.J. et al. (1991) "Isolation of Three Novel Human Cyclins by Rescue of G1 Cyclin (Cln) Function in Yeast" *Cell*, vol. 66, pp. 1197-1206.

Matsushime, H. et al. (1991) "Colony-Stimulating Factor 1 Regulates Novel Cyclins during the G1 Phase of the Cell Cycle" *Cell*, vol. 65, pp. 701-713.

Matsushime, H. et al. (1992) "Identification and Properties of an Atypical Catalytic Subunit (p34*PSK-J3* /cdk4) for Mammalian D Type G1 Cyclins" *Cell*, vol. 71, pp. 323-334.

Motokura, T. et al. (1991) "A novel cyclin encoded by a *bcl1*-linked candidate oncogene" *Nature*, vol. 350, pp. 512-515.

Mowat, M. et al. (1985) "Rearrangements of the cellular p53 gene in erythroleukaemic cells transformed by Friend virus" *Nature*, vol. 314, pp. 633-636.

Paris, J. et al. (1994) "Study of the higher eukaryotic gene function CDK2 using fission yeast" *Journal of Cell Science*, vol. 107, pp. 615-623.

Pines, J. and Hunter, T. (1990) "Human cyclin A is adenovirus E1A-associated protein p60 and behaves differently from cyclin B" *Nature*, vol. 346, pp. 760-763.

Potashkin, J.A. and Beach, D.H. (1988) "Multiple phosphorylated forms of the product of the fission yeast cell division cycle gene $cdc2^+$" *Current Genetics*, vol. 14, pp. 235-140.

Serrano, M. et al. (1993) "A new regulatory motif in cell-cycle control causing specific inhibition of cyclin D/CDK4" *Nature*, vol. 366, pp. 704-707.

Sherr, C.J. (1993) "Mammalian $G_1$ Cyclins" *Cell*, vol. 73, pp. 1059-1065.

Walker, G.J. et al. (1994) "Refined localization of the melanoma (MLM) gene on chromosome 9p by analysis of allelic deletions" *Oncogene*, vol. 9, pp. 819-824.

Wang, J. et al. (1990) "Hepatitis B virus integration in a cyclin A gene in a hepatocellular carcinoma" *Nature*, vol. 343, pp. 555-557.

Weinberg, R.A. (1988) "Finding the Anti-Oncogene" *Scientific American*, vol. 259, No. 3, pp. 44-51.

Xiong, Y. et al (1992) "D Type Cyclins Associate with Multiple Protein Kinases and the DNA Replication and Repair Factor PCNA" *Cell*, vol. 71, pp. 505-514.

Xiong, Y. et al. (1991) "Human D-Type Cyclin" *Cell*, vol. 65, pp. 691-699.

Xiong, Y. et al. (1992) "Molecular Cloning and Chromosomal Mapping of *CCND* Genes Encoding Human D-Type Cyclins" *Genomics*, vol. 13, pp. 575-584.

Xiong, Y. et al. (1993) "p21 in a universal inhibitor of cyclin kinases" *Nature*, vol. 366, pp. 701-704.

Xiong, Y. et al. (1993) "Subunit rearrangement of the cyclin-dependent kinases is associated with cellular transformation" *Genes & Development*, vol. 7, pp. 1572-1583.

Zhang, H. et al. (1993) "Proliferating Cell Nuclear Antigen and p21 Are Components of Multiple Cell Cycle Kinase Complexes" *Molecular Biology of the Cell*, vol. 4, pp. 897-906.

Chan, F.K.M. et al. "Identification of Human and Mouse p19, a Novel CDK4 and CDK6 Inhibitor with Homology to p16INK4" *Mol. Cell Biol.*, vol. 15, pp. 2682-2688 (1995).

Guan, K.-L. et al. "Growth Suppression by p18, A p16INK4/MTS1- and p14INK4b/MTS2-Related CDK6 Inhibitor, Correlates with Wild Type pRb Function" *Genes & Development*, vol. 8, pp.2939-2952 (1994).

Hannon, G.J. and Beach, D. "p15INK4B is a Potential Effector of TGF-beta-induced Cell Cycle Arrest"*Nature*, vol. 371, pp. 257-261 (1994).

Nobori, T. et al. "Deletions of the Cyclin-Dependent Kinase-4 Inhibitor Gene in Multiple Human Cancers" *Nature*, vol. 368, pp. 753-756. (1994).

\* cited by examiner

```
    Ex12                                    NTp16.2
CGGAGAGGGAATTCGGCACGAGGCAGCATGGAGCCTTCGGCTGACT
                                  Ex1
GGCTGGCCACGGCCGCGGCCCGGGGTCGGGTAGAGGAGGTGCGGGC
                              Ex13
GCTGCTGGAGGCGGTGGCGCTGCCCAACGCACCGAATAGTTACGGT
  NTp16.3                                    Ex14
CGGAGGCCGATCCAGGTCATGGATGATGGGCAGCGCCCGAGTGGC
            Ex2
GGAGCTGCTGCTGCTCCACGGCGCGGAGCCCAACTGCGCCGACCCC
         p16INT
GCCACTCTCACCCGACCCGTGCACCACGCTGCCCGGGAGGGCTTCT
        NTp16.5
GGACACGCTGGTGGTGCTGCACCGGGCCGGGGCGCGGCTGGACGTG
              Ex3
CGCGATGCCTGGGGCCGTCTGCCCGTGGACCTGGCTGAGGAGCTGG

GCCATCGCGATGTCGCACGGTACCTGCGCGCCCGTGCGGGGGGCAC
                          Ex15
CAGAGGCAGTAACCATGCCCGCATAGATGCCGCGGAAGGTCCCTCA
    Ex8                 Ex4
GACATCCCCGATTGAAAGAACCAGAGAGGCTCTGAGAAACCTCGGG
        Ex5
AAACTTAGATCATCAGTCACCGAAGGTCCTACAGGGCCACAACTGC

CCCCGCCACAACCCACCCCGCTTTCGTAGTTTTCATTTAGAAAATA

GAGCTTTTAAAAATGTCCTGCCTTTTAACGTAGATATAAGCCTTCC

CCCACTACCGTAAATGTCCATTTATATCATTTTTTATATATTCTTA

TAAAAATGTAAAAAGAAAACACCGCTTCTGCCTTTTCACTGTGTT
```

*Figure 1A*

```
                    Ex6
GGAGTTTTCTGGAGTGAGCACTCACGCCCTAAGCGCACATTCATGT

GGGCATTTCTTGCGAGCCTCGCAGCCTCCGGAAGCTGTCGACTTCA
              Ex7
TGACAAGCATTTTGTGAACTAGGGAAGCTCAGGGGGGTTACTGGCT

TCTCTTGAGTCACACTGCTAGCAAATGGCAGAACCAAAGCTCAAAT

AAAAATAAAATTATTTTCATTCATTCACTCAAAAAAA
```

*Figure 1B*

```
p16ex1    < GGNGGNAAGNTGTGGGGGAAAGTTTGGGGATGGAANACCAANCCCTCCTTTCNTTACCAA
            .........+.........+.........+.........+.........+.........+ p16ex1    < ACNCTGGCTCTGNCGAGGCTNCNTCCGANTGGTNCCCCCGGGGGAGACCCAACCTGGGNC
p16ex1    < GACTTCAGGGNTGCNACATTCACTAAGTGCTNGGAGNTAATANCACCTCCTCCGAGCANx
p16ex13                  TCNCTTATTGNTAGGANATAATAACACCTCCACCGATAACT
            .........+.........+.........+.........+.........+.........+ p16ex1    < TCGCTCACAGCGTCCCCTTACCTNGANAGATACCNCGXGXTCCCTCCAGAGGATTTGAGG
p16ex13   < TCACTTACAACGTCCCNNTTCCTGGAAAGATACACAGCGTTCCCTCCAGAGGATTTGTGG
            .........+.........+.........+.........+.........+.........+ p16ex1    < GACAGGNTCGGAGGGGGCTCTTCCCCCANCACCGGAGGAAGAAAGAGGAGGGNCTGACTG
p16ex13   < GACAGGGTNGGAGNGGTCTCTTCCNCCACCACCGGAGGAAGAAAGAGGAGGGGCTGNCTG
            .........+.........+.........+.........+.........+.........+

-----Ex1A--(12)-->
p16ex1    < GTCACCAGAGGGTGGGACGGACCGCGTGCGCTCGGCGNCTNCGGAGAGGGGGAGAACAGA
p16ex13   < TTCACCAGAGGGTGGGACGGACCNCGTACGCTCGNCGNCTNCGGAGAGGGGGAGAGCAGT
            .........+.........+.........+.........+.........+.........+ p16ex1    < CAACGGGCGGCGGGGAGCAGCATGGATCCGGCGGCGGGGAGCAGCATGGANCCTTCGACT
p16ex13   < CANCGGNCGNCGGGGAGCAACATGGAACCGNCGGCGGGGAGCAGCATGGANCCTTCGGCT
            .........+.........+.........+.........+.........+.........+ p16NT2    <                GACNNNCTCCGGCCGGNGTCGGGTAGAGGAGGTGCGGGCGCTGCTGGAG
p16ex1    < GACTGACTGCCTCGC
p16ex13   < GACTGGCTGNCCACGNCCACGNCCCGGGGTCGGGTAGAGGAGGTGCGGNCGCTNCTGGAG
            .........+.........+.........+.........+.........+.........+

<---------Ex13----------
p16nt3    >                                                 CTCTNANCCCGGGTA
p16nt2    < GCGGGGGCGCTGCCCAACGCACCGAATAGTTACGGTCGGAGGCCGATCCAGGTXXGGGTA
p16ex13   < GCGGGGNCTCTGNCCAACNCGCTAAAAN
            .........+.........+.........+.........+.........+.........+ p16nt3    > GAGGGTCTGCAGCGGGAGCAGNGGATGGCGGGCGACTCTGGAGGACGAAGTTGGCAGGGG
p16nt2    < GAGGGTCTGCAGCGGGAGCAGGGGATGGCGGGCGACTCTGGAGGACGAAGTTTGCAGGGG
            .........+.........+.........+.........+.........+.........+

<----------Ex1B------
p16nt3    > AATTGGAATCAGGTAGCGCTTCGANTCTCCGGAAAAAGGGGAGGCTTCCTGGGGAGTTNN
p16nt2    < AATTGGAATCAGGTAGCGCTTCGATTCTCCNGAAAAAGGGGAGGCTTCCTGGGGAGTTTT
```

*Figure 2A*

```
              .........+.........+.........+.........+.........+.........+
p16nt3   >   CAGAAGGGGTTTGTAATCACAGNCCTCCNCCTGGCGACGCCCTGGGGGGTTGGGAAGCCA
p16nt2   <   CAGAAGGGGTTTGTAATCACAGACCTCCTCCTGGCGACGTCCTGGGGGCTTGGGAAGCCA

.........+.........+.........+.........+.........+.........+
p16nt3   >   AGGAAGAGGAATGAGGAGNCACGCGCNTACAGNTCTCTCGAATNCTGANAAGATCTGAAG
p16nt2   <   AGGAAGAGGAATNAGGAGCCACGCGCGTACAGATCTCTCGAATGCTGAGAAGATCTNAAG

.........+.........+.........+.........+.........+.........+
p16nt3   >   GGGGGAACATATTTGTATTAGxATNNAAGTATGCTCTTTATCAGATACAAAATTCACGAA
p16nt2   <   GGGGGAACATATTTGTATTAGCNTCCAAGTNTNCTCTNTATCANATACAAANTxC

.........+.........+.........+.........+.........+.........+
p16nt3   >   CGTGTGGNATAAAAAGGGAGTCTTAAAGAAATNTAAGATGTGCTGGGACTACTTAGCCTC
p16nt3   >   CAANACACAGATNCCTGGATGGAGCT
```

*Figure 2B*

```
p16int   >  AAAANNAAAAAAAATCTCCCAGGCCTAACATAATTNTCAGGAAAGAAATTTCAGTAGTTG
            .........+.........+.........+.........+.........+.........+
p16int   >  NATCTCAGGGGAAATACAGGAAGTTAGCCTGGAGTAAAAGTCAGTCTGTCCCTGCCCCTT
            .........+.........+.........+.........+.........+.........+
p16int   >  TGCTANATTGCCCGTGCCTCACAGTGCTCTCTGCCTGTGACGACAGCTCCNCAGAAGTTC
            .........+.........+.........+.........+.........+.........+
p16int   >  GGAGGATATAATGGAATTCATTGTGTACTGAAGAATGGATAGAGAACTCAAGAAGGAAAT
            .........+.........+.........+.........+.........+.........+
p16int   >  TGGAAACTGGAAGCAAATGTAGGGGTAATTAGACACCTGGGGCTTGTGTGGGGGTCTGCT
p16ex15  <                                         AANAAAAAAGAAATNGATAANATAGAGGAT
            .........+.........+.........+.........+.........+.........+
                      ----------EX2A------->
p16int   >  TGGCGGTGAGGGGGCTCTACACAAGCTTCCTTTCCGTCATGCCGNCCCCCACCCTGGCGTC
p16ex15  <  GAACANATTAAAATCAAAAAACANAACANAGACATAATAAAAAACGAGAATGTTCTAGAC
            .........+.........+.........+.........+.........+.........+
                                                          ------EX14-------
p16int   >  TGACCATTCTGTTCTCTCTGGCAGGTCATGATGATGGGCAGCGCCCGAGTGGCGGAGCTG
p16ex15  <  NTAATCATAATTATAAAGGTCAAGACTCATTGATATnAAGGAAATTGAAGGGAAATCTTA
            .........+.........+.........+.........+.........+.........+
                    ->
p16int   >  CTGCTGCTCCACGGCGCGGAGCCCAACTGCTCCGACGCCG
p16ex2   >                                          CCTGCNACGACCCCGCCACTCTCACCCGACCCGTG
p16ex14  >             NCTCTCACGGTGGGGAGGCCAACTGCGCCGAACCCGCCACTCTCACCCGACCCGCG
p16ex15  <  ACTAGCACAANNGNATNAAAAAANAATTCCCACGACACCGCCACTCTCAACGCATCCGTG
            .........+.........+.........+.........+.........+.........+
p16ex2   >  CACGACGCTGTCCGGGAGGGTTTCCTGGACACGCTGGTGGTGCTGCACCGGGCCGGGGNG
p16ex14  >  CACGACGGTGCCCGGGAGGGGTTCCTGGACACGCTGGTGGTGCTGCACCGGGCCGGGGCG
p16ex15  <  CTCGACACTGCCCGGGAGGTCNTCCTGGACACGCTGGTGGTNCTCCACCGGNCCGGGGCA
            .........+.........+.........+.........+.........+.........+
p16ex2   >  CGGTTGGACGTGCGCGATGCCTGGGGCCGCCTNCCCGTGGXACCTGGTTGAGGAGCTGGG
p16ex14  >  CGGCTGGACGTTCGNGATGCCTGGGGGCNTCTNTCCGTNGXACCTGGCTGAAGAGCTGGN
p16ex15  <  CGTCTGGACGTGCGCGATGCCTGGGNCCGNCTACCCGTGGTACCTGACTGAGGACCTGGG
            .........+.........+.........+.........+.........+.........+
p16ex2   >  NCATCGCGATGTCGCACGGTACCTGCGCGCGGTTGCGGGGGGCACCAGAGGXNAGTNACC
p16ex14  >  NCATCGNGATGTCGCACGGCCNTGTGTGNGGNTGCGGGGGGCACCATAGGTCAGTNTCC
p16ex15  <  CCATCCCGATTTCGCNGGGTANCTGNGNGNGGCTGNGGGGGCCAANAGAGGXCANTACCC
```

*Figure 2C*

```
P16EX5  <  XAAGTATGAGCGAAACNAATTGTGGTTTGAGAANAGGNAATCGTAGGGAACTTCGGGATC
           .........+.........+.........+.........+.........+.........+

P16EX5  <  CCNCNGGGANCNCCAGAACCTGAGNCGCCNATTGGAAATNACAAACTGNCTGNATCACTC
           .........+.........+.........+.........+.........+.........+

P16EX5  <  CGNACCAGGTNCAAAAGATACCTGGGGANGCGGGAAGGGAAAGACNACATCNAGACCGCC
P16EX9  <                                                          CCCC
           .........+.........+.........+.........+.........+.........+

P16EX5  <  TTCGCNCCTXGGNATTGTGAGCAGCCTCTGAGACTCATTXATATNACACTCGTXTTTCTT
P16EX9  <  ATCGCGCCTTGGGANTGTGAGCNACCATTGAGACTCATNAATATAGCACTCGTTTTTCTT
           .........+.........+.........+.........+.........+.........+

P16EX5  <  CTTACAACCCTGCGGNCCGCGCGGTCGCGCTTTCTCTGCCCTCCGCCGGGTGGACCTGGA
P16EX9  <  CTTGCAACCCTGCGGNCCGCGCGGTCGCGCTNTCTCTGCCCTCCGCNGGGTGGACCTGGA
           .........+.........+.........+.........+.........+.........+

P16EX5  <  GCGCTTGAGCGGTCGGCGCGCCTGGAGCAGCCAGGCGGNCAGTGGACTAGCTGCTGGACC
P16EX9  <  GCGCTTGAGCGGTCGGCGCNCCTGGANCAGCCAGGCGGGCAGTGGACTACCTNCTGGACC
           .........+.........+.........+.........+.........+.........+

P16EX5  <  AGGGAGGTGTGGGAGAGCGGTGGCGGCGGGTACATGCACGTGAAGCCATTGCGAGAACTT
P16EX9  <  AGGGAGGTGTGGGAGAGCGGTGNCGGCGGGTACATGCACGTGAAGCCATTGCGAGAACTT
           .........+.........+.........+.........+.........+.........+

P16EX5  <  TATCCATAAGTATTTCAATACCGGTAGGGACGGCAAGAGAGGAGGGCGGGATGTGCCACA
P16EX5  <  TATCCATAAGTATTTCAATGCCGGTAGGGACGGCAAGAGAGGAGGGCGGGATGTNCCACA
           .........+.........+.........+.........+.........+.........+

P16EX5  <  CATCTTTGACCTCAGGTTTCTAACGCCTGTTTTCTTTCTGCCCTCTGCAGACAACCCCGA
P16EX9  <  CATCTTTGACCTCAGGTTTCTAACGCCTGTTTTCTTTCTGCCCTCTGCAGACATCCCCGA
           .........+.........+.........+.........+.........+.........+

P16EX4  >                                              AGAAATTAGATCATCAGTCACCGATG
P16EX5  <  TTGAAAGAACCAGAGAGGCTCTGAGAAACC
P16EX9  <  TTGAAAGAACCAGAGAGGCTCTGAGAAACCTCCGGAAACTTAGXTCATCAXTCGCCGNAA
           .........+.........+.........+.........+.........+.........+

P16EX4  >  GTCCTACAGGGNCACAACTGNCCCCGCCACAACCCACCCCGNTTTCGTAGTTTTCATTTA
P16EX9  <  AA
```

*Figure 3A*

```
P16EX4   > GAAAATAGAGCTTTTAAAAATGTCCTGCCTTTTAACGTAGATATATGCCTTCCCCCACTA
           .........+.........+.........+.........+.........+.........+

P16EX4   > CCGNAAATGTCCATTTATATCATNTTTTATATATTCTTATAAAAATGTAAAAAAGAAAAA
           .........+.........+.........+.........+.........+.........+

P16EX4   > CACCGCTTCTGCCTTTTCACTGTGTTGGAGTTTTCTGGAGTGAGCACTCACGCCCTAAGC
           .........+.........+.........+.........+.........+.........+

P16EX6   >   CANCNATNTNCGGCATTTCTNGNGAGCCTCGTAGTCTCCGGATGNTGTCGACCTCGAG
P16EX6A  >   CANCNATNTNCGGCATTTCTNGNGAGCCTCGTAGTCTCCGGATGNTGTCGACCTCGAG
P16EX4   > GCACATTCATGTGGGCATTTCTTGCGAGCCTCGCAGNCTCCGGAAGCTGTCGACCTCGAG
           .........+.........+.........+.........+.........+.........+

P16EX6   > GGGGGGNCCNGTACCCAATTCGNCCTATNGTGAGTCGTNTTACAATTCACTGGCCGCCGT
P16EX6A  > GGGGGGNCCNGTACCCAATTCGNCCTATNGTGAGTCGTNTTACAATTCACTGGCCGCCGT
P16EX4   > GGGGGGNCCGGTACCCAATTCGCCCTATAGTGAGTCGTATTACAATTCACTGGNCGNCGN
           .........+.........+.........+.........+.........+.........+

P16EX6   > TTTXACAACGTCGXTGXACTGGGAAAACCCTGGTGTTACCCAACTTXAATCGCCTTGNAG
P16EX6A  > TTTXACAACGTCGXTGXACTGGGAAAACCCTGGTGTTACCCAACTTXAATCGCCTTGNAG
P16EX4   > TTTTACAACGTCGGTGGACTGGGAAAACCCCGGNGTTACCCAACTTTAATCGNCTTGGAG
           .........+.........+.........+.........+.........+.........+

P16EX6   > NACATCCCCCTTTXCGCCAGCTGGTGTAATAGCGANGAGGCCCGCACCGATCGCCCTTCC
P16EX6A. > NACATCCCCCTTTXCGCCAGCTGGTGTAATAGCGANGAGGCCCGCACCGATCGCCCTTCC
P16EX4   > GACATCCCCCTTTTCGCCAGNTGGGGTTATAGNGAAGAGGGCCNCACCNNTCGCCC
           .........+.........+.........+.........+.........+.........+

P16EX6   > CAACAGTTGNGCAGCCTGAATGGCGAATGGAAATTGTAAGCGTTAATATTTTGTTAAAAT
P16EX6A  > CAACAGTTGNGCAGCCTGAATGGCGAATGGAAATTGTAAGCGTTAATATTTTGTTAAAAT
           .........+.........+.........+.........+.........+.........+

P16EX6   > TCGCGTTANATCNTCGGTTAANTCAGCTCATNTTTTATCCAATAGGCCGANATCGGCANA
P16EX6A  > TCGCGTTANATCNTCGGTTAANTCAGCTCATNTTTTATCCAATAGGCCGANATCGGCANA
           .........+.........+.........+.........+.........+.........+

P16EX6   > ATCCCCAATAAATCAANAGAATAGACCGAGATAGGGTTGAGTGTCGTTCCAGTTNGGGAA
P16EX6A  > ATCCCCAATAAATCAANAGAATAGACCGAGATAGGGTTGAGTGTCGTTCCAGTTNGGGAA
           .........+.........+.........+.........+.........+.........+

P16EX6   > CANGAGTCCACTATTAAAGANCGTAGNCTCNAACGTCANAGGGCGAAAAACCNTNTTTCA
P16EX6A  > CANGAGTCCACTATTAAAGANCGTAGNCTCNAACGTCANAGGGCGAAAAACCNTNTTTCA
```

*Figure 3B*

```
         .........+.........+.........+.........+.........+.........+
P16EX6  > GNGGATTGGNCCACTACGCNTANCC
P16EX6A > GNGGATTGGNCCACTACGCNTANCCATCACCCTATTC
```

| cell | H9 | U18 | CCL119 | MCF-7 | HTB 125 | SaOs2 | A431 | normal #1 | normal #2 |
|---|---|---|---|---|---|---|---|---|---|
| exon 1 | absent | absent | absent | absent | absent | altered | altered | norm | norm |
| exon 2 | absent | absent | absent | absent | absent | altered | absent | norm | norm |

| cell | WI38 | CCL120 | HeLa | HTB100 | ZRB75 | GM130 | Tera2 | HTB172 | HTB173 |
|---|---|---|---|---|---|---|---|---|---|
| exon 1 | norm | norm | norm | norm | norm | norm | norm | norm | norm |
| exon 2 | norm | norm | norm | norm | norm | norm | norm | norm | norm |

P16$^{INK4}$ POLYPEPTIDES

RELATED APPLICATIONS

This application claims priority to Patent Cooperation Treaty Application No. PCT/US93/09945, filed Oct. 18, 1993, which is a continuation-in-part of U.S. Ser. No. 07/963,308 (now abandoned), filed Oct. 16, 1992, and U.S. Ser. No. 07/991,997 (now abandoned), filed Dec. 17, 1992. This application is a continuation-in-part of U.S. Ser. No. 08/154,915 (now abandoned), filed Nov. 18, 1993, which is a continuation-in-part of U.S. Ser. No. 07/991,997 (now abandoned), filed Dec. 17, 1992, which is a continuation-in-part of U.S. Ser. No. 07/963,308 (now abandoned), filed Oct. 16, 1992, which is a continuation-in-part of U.S. Ser. No. 07/888,178 (now abandoned), filed May 26, 1992, which is a continuation in part of U.S. Ser. No. 07/701,514 (now abandoned), filed May 16, 1991. The teachings of U.S. Ser. Nos. 08/154,915, 07/991,997, 07/963,308, 07/888,178, 07/701,514 and PCT/US93/09945 are incorporated herein by reference.

FUNDING

Work described herein was supported by National Institutes of Health Grant and the Howard Hughes Medical Institute under NIH Grant No. R01GM39620. The United States Government has certain rights in the invention.

BACKGROUND OF THE INVENTION

Neoplasia is characterized by deregulated cell growth and division. Inevitably, molecular pathways controlling cell growth must interact with those regulating cell division. It was not until very recently, however, that experimental evidence became available to bring such connection to light. Cyclin A was found in association with the adenovirus oncoprotein E1A in virally transformed cells (Giordona et al. *Cell* 58:981 (1989); and Pines et al. *Nature* 346:760 (1990)). In an early hepatocellular carcinoma, the human cyclin A gene was found to be the integration site of a fragment of the hepatitis B virus, which leads to activation of cyclin A transcription and a chimeric viral cyclin A protein that is not degradable in vitro (Wang et al. *Nature* 343:555 (1990)). The cell cycle gene implicated most strongly in oncogenesis thus far is the human cyclin D1. It was originally isolated through genetic complementation of yeast $G_1$ cyclin deficient strains (Xiong et al. *Cell* 65:691(1991); and Lew et al. *Cell* 66:1197 (1991)), as cellular genes whose transcription is stimulated by CSF-1 in murine macrophages (Matsushine et al. *Cell* 65:701 (1991)) and in the putative oncogene PRAD1 rearranged in parathyroid tumors (Montokura et al. *Nature* 350:512 (1991). Two additional human D-type cyclins, cyclins D2 and D3, were subsequently identified using PCR and low-stringency hybridiazation techniques (Inaba et al. *Genomics* 13:565 (1992); and Xiong et al. *Genomics* 13:575 (1992)). Cyclin D1 is genetically linked to the bcl-1 oncogene, a locus activated by translocation to an immunoglobulin gene enhancer in some B-cell lymphomas and leukemias, and located at a site of gene amplification in 15-20% of human breast cancers and 25-48% of squamous cell cancers of head and neck origin.

However, the creation of a mutant onocogene is only one of the requirements needed for tumor formation; tumorigenesis appears to also require the additional inactivation of a second class of critical genes: the "anti-oncogenes" or "tumor-suppressing genes." In their natural state these genes act to suppress cell proliferation. Damage to such genes leads to a loss of this suppression, and thereby results in tumorigenesis. Thus, the deregulation of cell growth may be mediated by either the activation of oncogenes or the inactivation of tumor-suppressing genes (Weinberg, R. A., (September 1988) *Scientific Amer*. pp 44-51).

Oncogenes and tumor-suppressing genes have a basic distinguished feature. The oncogenes identified thus far have arisen only in somatic cells, and thus have been incapable of transmitting their effects to the germ line of the host animal. In contrast, mutations in tumor-suppressing genes can be identified in germ line cells, and are thus transmissible to an animal's progeny.

The classic example of a hereditary cancer is retinoblastomas in children. The incidence of the retinoblastomas is determined by a tumor suppressor gene, the retinoblastoma (Rb) gene (Weinberg, R. A., (September 1988) *Scientific Amer*. pp 44-51; Hansen et al. (1988) *Trends Genet* 4:125-128). Individuals born with a lesion in one of the Rb alleles are predisposed to early childhood development of retinoblastomas. Inactivation or mutation of the second Rb allele in one of the somatic cells of these susceptible individuals appears to be the molecular event that leads to tumor formation (Caveneee et al. (1983) *Nature* 305:799-784; Friend et al. (1987) *PNAS* 84:9059-9063).

The Rb tumor-suppressing gene has been localized onto human chromosome 13. The mutation may be readily transmitted through the germ line of afflicted individuals (Cavenee, et al. (1986) *New Engl. J. Med* 314:1201-1207). Individuals who have mutations in only one of the two naturally present alleles of this tumor-suppressing gene are predisposed to retinoblastoma. Inactivation of the second of the two alleles is, however, required for tumorigenesis (Knudson (1971) *PNAS* 68:820-823).

A second tumor-suppressing gene is the p53 gene (Green (1989) *Cell* 56:1-3; Mowat et al (1985 *Nature* 314:633-636). The protein encoded by the p53 gene is a nuclear protein that forms a stable complex with both the SV40 large T antigen and the adenovirus E1B 55 kd protein. The p53 gene product may be inactivated by binding to these proteins.

Based on cause and effect analysis of p53 mutants, the functional role of p53 as a "cell cycle checkpoint", particularly with respect to controlling progression of a cell from G1 phase into S phase, has implicated p53 as able to directly or indirectly affect cycle cyle machinery. The first firm evidence for a specific biochemical link between p53 and the cell cycle comes a finding that p53 apparently regulates expression of a second protein, p21, which inhibits cyclin-dependent kinases (cdks) needed to drive cells through the cell cycle, e.g. from G1 into S phase. For example, it has been demonstrated that non-viral transformation, such as resulting at least in part from a mutation of deletion of of the p53 tumor suppressor, can result in loss of p21 from cyclin/cdk complexes. As described Xiong et al. (1993) *Nature* 366:701-704, induction of p21 in response to p53 represents a plausible mechanism for effecting cell cycle arrest in response to DNA damage, and loss of p53 may deregulate growth by loss of the p21 cell-cycle inhibitor.

SUMMARY OF THE INVENTION

The present invention relates to the discovery in eukaryotic cells, particularly human cells, a novel polypeptide of 16 kDa (hereinafter "p16$^{INK4}$" or "p16") can function as an inhibitor of cell cycle progression, and therefore ultimately of cell growth, and that similar to role of p21 and p53, the p16 protein may function coordinately with the cell cycle regulatory protein, retinoblastoma (Rb).

One aspect of the invention features a substantially pure preparation of a p16$^{INK4}$ polypeptide, or a fragment thereof, which specifically binds a cyclin-dependent kinase (cdk), wherein the p16$^{INK4}$ polypeptide having an approximate molecular weight of 16 kD. In a preferred embodiment: the polypeptide has an amino acid sequence at least 60% homologous to the amino acid sequence of SEQ ID No. 2; the polypeptide has an amino acid sequence at least 80% homologous to the amino acid sequence of SEQ ID No. 2; the polypeptide has an amino acid sequence at least 90% homologous to the amino acid sequence of SEQ ID No. 2; the polypeptide has an amino acid sequence identical to the amino acid sequence of SEQ ID No. 2. In a preferred embodiment: the fragment comprises at least 5 contiguous amino acid residues of SEQ ID No. 2; the fragment comprises at least 20 contiguous amino acid residues of SEQ ID No. 2; the fragment comprises at least 50 contiguous amino acid residues of SEQ ID No. 2.

Another aspect of the present invention features a p16$^{INK4}$ polypeptide which functions in one of either role of an agonist of cell-cycle regulation or an antagonist of cell-cycle regulation. In a preferred embodiment: the p16$^{INK4}$ polypeptide specifically binds a cyclin dependent kinase (cdk), e.g. specifically binds cdk4; e.g. specifically binds cdk6; e.g. inhibits a kinase acitivity of cdk4; inhibits a kinase acitivity of cdk6; e.g. inhibits phosphorylation of an Rb protein by cdk4. In a more preferred embodiment: the p16$^{INK4}$ polypeptide regulates a eukaryotic cell cycle, e.g. a mammalian cell cycle, e.g., a human cell cycle; the p16$^{INK4}$ polypeptide inhibits proliferation/cell growth of a eukaryotic cell, e.g., a human cell; the p16$^{INK4}$ polypeptide inhibits progression of a eukaryotic cell from G1 phase into S phase, e.g., inhibits progression of a mammalian cell from G1 phase into S phase, e.g., inhibits progression of a human cell from G1 phase into S phase; the p16$^{INK4}$ polypeptide inhibits the kinase activity of a cyclin dependent kinase (cdk), e.g. a cdk active in G1 phase, e.g. cdk 4; the p16$^{INK4}$ polypeptide suppresses tumor growth, e.g. in a tumor cell, e.g. in a tumor cell having an unimpaired Rb protein.

Yet another aspect of the present invention concerns an immunogen comprising a p16$^{INK4}$ polypeptide, or a fragment thereof, in an immunogenic preparation, the immunogen being capable of eliciting an immune response specific for said p16$^{INK4}$ polypeptide; e.g. a humoral response, eg. an antibody respone; e.g. a cellular response.

A still further aspect of the present invention features an antibody preparation specifically reactive with an epitope of the p16$^{INK4}$ immunogen.

Another aspect of the present invention features recombinant p16$^{INK 4}$ polypeptide, or a fragment thereof, having an amino acid sequence preferably: at least 60% homologous to SEQ ID NO. 2; at least 80% homologous to SEQ ID No. 2; at least 90% homologous to SEQ ID No. 2; at least 95% homologous to SEQ ID No. 2. In a preferred embodiment, the recombinant p16 protein functions in one of either role of an agonist of cell cycle regulation or an antagonist of cell cycle regulation. In a more preferred embodiment: the p16$^{INK4}$ polypeptide specifically binds a cyclin dependent kinase (cdk), e.g. specifically binds cdk4; e.g. specifically binds cdk6; e.g. inhibits a kinase acitivity of cdk4; inhibits a kinase acitivity of cdk6; e.g. inhibits phosphorylation of an Rb protein by cdk4. In a more preferred embodiment: the p16$^{INK4}$ polypeptide regulates a eukaryotic cell cycle, e.g. a mammalian cell cycle, e.g., a human cell cycle; the p16$^{INK4}$ polypeptide inhibits proliferation/cell growth of a eukaryotic cell, e.g., a human cell; the p16$^{INK4}$ polypeptide inhibits progression of a eukaryotic cell from G1 phase into S phase, e.g., inhibits progression of a mammalian cell from G1 phase into S phase, e.g., inhibits progression of a human cell from G1 phase into S phase; the p16$^{INK4}$ polypeptide inhibits the kinase activity of a cyclin dependent kinase (cdk), e.g. a cdk active in G1 phase, e.g. cdk 4; the p16$^{INK4}$ polypeptide suppresses tumor growth, e.g. in a tumor cell, e.g. in a tumor cell having an unimpaired Rb protein.

The recombinant p16 protein preferably comprises: at least 5 contiguous amino acid residues of SEQ ID No. 2; at least 20 contiguous amino acid residues of SEQ ID No. 2; at least 50 contiguous amino acid residues of SEQ ID No.2.

In yet other preferred embodiments, the recombinant p16 protein is a fusion protein further comprising a second polypeptide portion having an amino acid sequence from a protein unrelated the protein of SEQ ID No.2. Such fusion proteins can be functional in a two-hybrid assay.

Another aspect of the present invention provides a substantially pure nucleic acid having a nucleotide sequence which encodes a p16$^{INK4}$ polypeptide, or a fragment thereof, having an amino acid sequence at least 60% homologous to SEQ ID NO. 2. In a more preferred embodiment, the nucleic acid encodes a protein having an amino acid sequence at least 80% homologous to SEQ ID No. 2; more preferably at least 90% homologous to SEQ ID No. 2; and most preferably at least 95% homologous to SEQ ID No. 2. The nucleic preferably encodes a p16$^{INK4}$ polypeptide which specifically binds a cyclin dependent kinase (cdk); e.g. specifically binds cdk4; e.g. specifically binds cdk6; e.g. which inhibits a kinase activity of cdk4; e.g. which inhibits phosphorylation of an Rb protein by cdk4.

In yet a further preferred embodiment, the nucleic acid which encodes a p16$^{INK4}$ polypeptide, or a fragment thereof, hybridizes under stringent conditions to a nucleic acid probe corresponding to at least 12 consecutive nucleotides of SEQ ID No. 1; more preferably to at least 20 consecutive nucleotides of SEQ ID No. 1; more preferably to at least 40 consecutive nucleotides of SEQ ID No. 1.

Furthermore, in certain preferred embodiments, p16 nucleic acid will comprise a transcriptional regulatory sequence,e.g. at least one of a transcriptional promoter or transcriptional enhancer sequence, operably linked to the p16 gene sequence so as to render the p16 gene sequence suitable for use as an expression vector.

The present invention also features transgenic non-human animals, e.g. mice, which either express a heterologous p16 gene, e.g. derived from humans, or which mis-express their own p16 gene, e.g. p16 expression is disrupted. Such a transgenic animal can serve as an animal model for studying cellular disorders comprising mutated or mis-expressed p16 allelles.

The present invention also provides a probe/primer comprising a substantially purified oligonucleotide, wherein the oligonucleotide comprises a region of nucleotide sequence which hybridizes under stringent conditions to at least 10 consecutive nucleotides of sense or antisense sequence of SEQ ID No. 1 or naturally occuring mutants thereof. In preferred embodiments, the probe/primer further comprises a label group attached thereto and able to be detected, e.g. the label group is selected from a group consisting of radioisotopes, fluorescent compounds, enzymes, and enzyme co-factors. Such probes can be used as a part of a diagnostic test kit for identifying transformed cells, such as for measuring a level of a p16$^{INK4}$ nucleic acid in a sample of cells isolated from a patient; e.g. measuring the p16 mRNA level in a cell; e.g. determining whether the genomic p16 gene has been mutated or deleted.

The present invention also provides an assay for screening test compounds for an inhibitor of an interaction of a p16$^{INK4}$ polypeptide with a cyclin dependent kinase (cdk) comprising the steps of (i) combining a cdk and a p16$^{INK4}$ polypeptide comprising an amino acid sequence SEQ ID No. 2, under conditions wherein the cdk and the p16$^{INK4}$ polypeptide are able to interact; (ii) contacting the combination with a test compound; and (iii) detecting the formation of a complex comprising said E6 protein and said cellular target protein. Wherein a decrease in the formation of said complex in the presence of said test compound is indicative of an inhibitor of the interaction between a cdk and a p16$^{INK4}$ polypeptide. In preferred embodiments: the cdk is cdk4; the cdk is cdk6; the cdk and the p16$^{INK4}$ polypeptide are combined in an cell-free system and contacted with said test compound; i.e. the cell-free system is selected from a group consisting of a cell lysate and a reconstituted protein mixture; the cdk and the p16$^{INK4}$ polypeptide are simultaneously expressed in a cell, and the cell is contacted with the test compound, e.g. the cdk and the p16 comprise an interaction trap assay (two hybrid assay).

The present invention also provides a method for treating an animal having unwanted cell growth characterized by a loss of wild-type p16$^{INK4}$ function, comprising administering a therapeutically effective amount of an agent able to inhibit a kinase activity of cdk4. IN preferred embodiments, the method comprises administering a nucleic acid construct encoding the polypeptide of SEQ ID No. 2, under conditions wherein the construct is incorporated by p16$^{INK4}$ deficient cells and the polypeptide of SEQ ID No. 2 is expressed, e.g. by gene therapy techniques.

Another aspect of the present invention provides a method of determining if a subject, e.g. a human patient, is at risk for a disorder characterized by unwanted cell proliferation, comprising detecting, in a tissue of the subject, the presence or absence of a genetic lesion characterized by at least one of (i) a mutation of a gene encoding a protein represented by SEQ ID No. 2, or a homolog thereof; or (ii) the mis-expression of the p16 gene. In preferred embodiments: detecting the genetic lesion comprises ascertaining the existence of at least one of a deletion of one or more nucleotides from said gene, an addition of one or more nucleotides to said gene, an substitution of one or more nucleotides of said gene, a gross chromosomal rearrangement of said gene, a gross alteration in the level of a messanger RNA transcript of said gene, the presence of a non-wild type splicing pattern of a messanger RNA transcript of said gene, or a non-wild type level of said protein. For example, detecting the genetic lesion can comprise (i) providing a probe/primer comprising an oligonucleotide containing a region of nucleotide sequence which hybridizes to a sense or antisense sequence of SEQ ID No. 1 or naturally occuring mutants thereof or 5' or 3' flanking sequences naturally associated with said gene; (ii) exposing said probe/primer to nucleic acid of said tissue; and (iii) detecting, by hybridization of said probe/primer to said nucleic acid, the presence or absence of said genetic lesion; e.g. wherein detecting the lesion comprises utilizing the probe/primer to determine the nucleotide sequence of the p16 gene and, optionally, of the flanking nucleic acid sequences; e.g. wherein detecting the lesion comprises utilizing the probe/primer in a polymerase chain reaction (PCR); e.g. wherein detecting said lesion comprises utilizing the probe/primer in a ligation chain reaction (LCR). In alternate embodiments, the level of said protein is detected in an immunoassay.

Other features and advantages of the invention will be apparent from the following detailed description, and from the claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press:1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

DESCRIPTION OF THE DRAWINGS

FIGS. 1A-B are a schematic representation of the p16 cDNA (SEQ ID No. 1), indicating the location of exon boundaries and PCR primers used in the present invention.

FIGS. 2A and 2B are the genomic nucleic acid sequence (SEQ ID Nos. 3-6) for exon 1 and the non-coding sequences directly flanking exon 1. The sequence is a composite sequence from several primers. FIG. 2C is the genomic sequence (SEQ ID Nos. 7-10) about exon 2.

FIGS. 3A-3C are the genomic nucleic acid sequence for exon 3 and the non-coding sequences directly flanking exon 3. The sequence is a composite sequence from several primers.

FIG. 4 illustrates the loss of p16 sequences from the genomes of several human tumor cells, as compared to normal human controls and other human tumors.

DETAILED DESCRIPTION OF THE INVENTION

Figure 5:
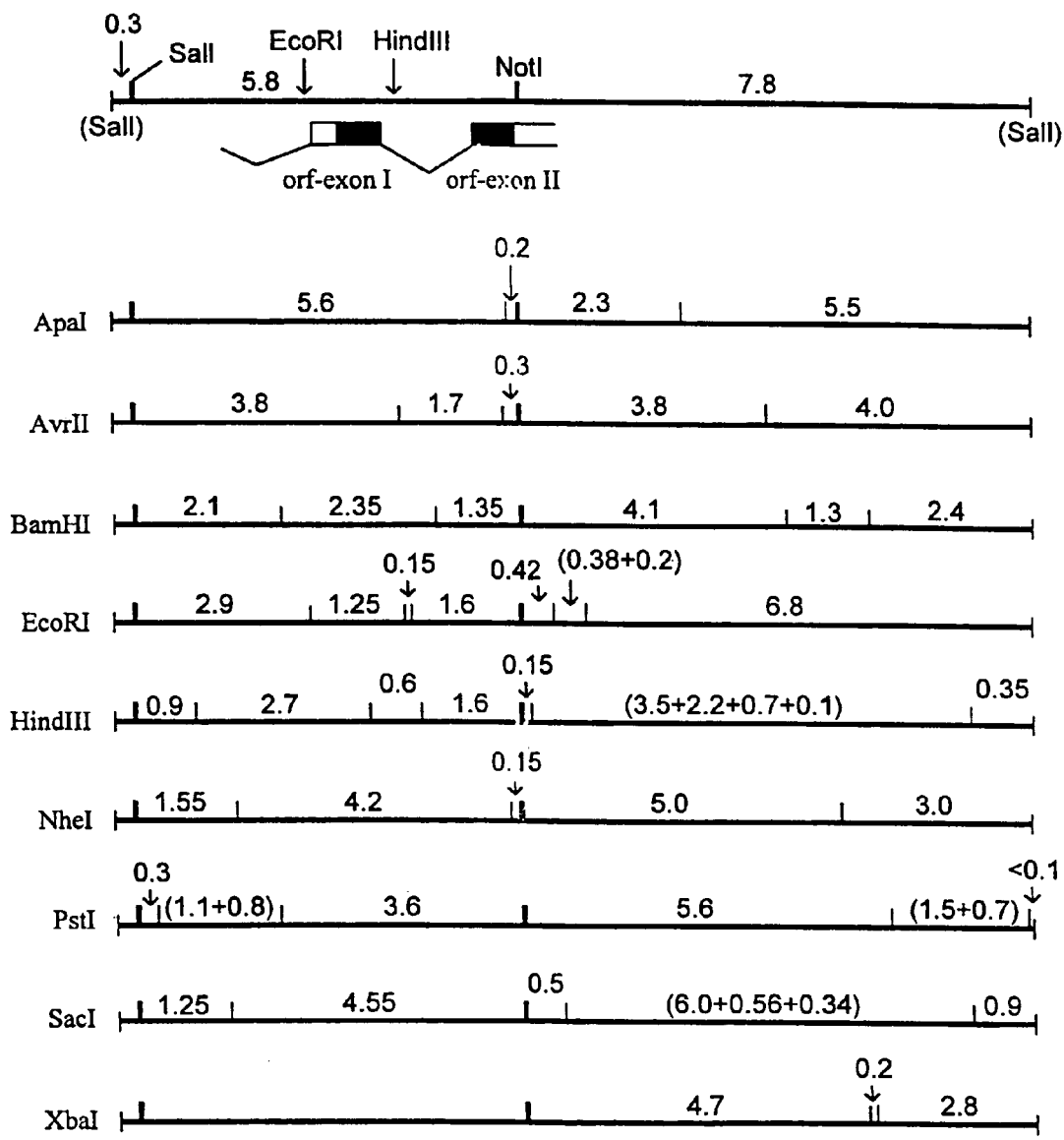
FIG. 5 illustrates the restriction map for the mouse p16 gene.

The present invention makes available diagnostic and therapeutic assays and reagents for detecting and treating transformed cells, such as may be useful in the detection of cancer. It is demonstrated below that cellular transformation is associated with selective deletion of a 16 Kd polypeptide (termed hereinafter "p16"). For example, the present invention makes available reagents, including antibodies and nucleic acid probes, for detecting altered complex formation and/or increased altered levels of p16 expression and/or p16 gene deletion or mutation, in order to identify transformed cells.

In addition, p16 is demonstrated below to exert an inhibitory effect on the activity of cyclin/CDK complexes, particularly those which include cdk4 or cdk6. For instance, p16 is able to inhibit the activity of cyclin D1/CDK complexes in vivo. As is generally known, cyclin D1 has been associated with a wide variety of proliferative diseases. Thus, the present invention identifies a potential inhibitor of cell proliferation resulting from oncogenic expression of cyclin D1.

Conversely, p16 can be used in assays to identify agents which decrease the ability of p16 to bind cdk4 and thereby relieve inhibition of cyclin/cdk4 complexes. In this embodiment, the reactivation of the cdk4/cyclin complexes disrupts or otherwise unbalances the cellular events occuring in a transformed cell. Such agents can be of use therapeutically to activate cdk4 complexes in cells transformed, for example, by tumor viruses. Treatment of such cells can result in enhancement of otherwise virally-suppressed cell-cycle checkpoints, such as p53, and results in the accumulation of the infected cell at the checkpoint, or alternatively, in the instance of Rb phosphorylation, cause premature progession through a checkpoint so as to result in cell death.

Accordingly, one aspect of this invention pertains to an isolated nucleic acid comprising the nucleotide sequence encoding a p16$^{INK4}$ protein, fragments thereof encoding polypeptides having at least one biological activity of a p16, and/or equivalents of such nucleic acids. The term nucleic acid as used herein is intended to include such fragments and equivalents. The term equivalent is understood to include nucleotide sequences encoding functionally equivalent p16 proteins or functionally equivalent peptides having an activity of a p16 protein such as described herein. Equivalent nucleotide sequences will include sequences that differ by one or more nucleotide substitutions, additions or deletions, such as allelic variants; and will also include sequences that differ from the nucleotide sequence encoding the presently claimed p16 protein shown in SEQ ID NO: 1 due to the degeneracy of the genetic code. Equivalents will also include nucleotide sequences that hybridize under stringent conditions (i.e., equivalent to about 20-27° C. below the melting temperature ($T_m$) of the DNA duplex formed in about 1 M salt) to the nucleotide sequence of the presently claimed p16 protein shown in SEQ ID NO: 1. In one embodiment, equivalents will further include nucleic acid sequences derived from and evolutionarily related to the nucleotide sequence shown in SEQ ID NO 1.

Polypeptides referred to herein as having an activity of a p16 protein are defined as peptides that have an amino acid sequence corresponding to all or a portion of the amino acid sequence of the p16 protein shown in SEQ ID NO: 2 and which have at least one biological activity of a p16 protein. In preferred embodiments, a biological activity of a p16 protein includes: an ability to regulate a eukaryotic cell cycle, e.g. a mammalian cell cycle, e.g., a human cell cycle; an ability to inhibit proliferation/cell growth of a eukaryotic cell, e.g. a mammalian cell, e.g., a human cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (cdk), e.g. a cdk active in G1 phase, e.g. cdk 4, e.g. cdk6, e.g. an ability to inhibit phosphorylation of an Rb protein by cdk4. P16 proteins of the present invention can also have biological activities which include an ability to suppress tumor growth e.g. in a tumor having an unimpaired Rb protein. Other biological activities of the subject p16 proteins are described herein or will be reasonably apparent to those skilled in the art. It will be generally appreciated that it can be advantageous to provide under various circumstances either p16 agonists or p16 antagonists, in order to either promote or inhibit only a subset of the biological activities of naturally occurring p16 proteins, in order that, for example, specific effects can be elicited by treatment with fewer potential side effects relative to agonists or antagonists directed to all p16-related biological activities.

The term "evolutionarily related to", with respect to nucleic acid sequences encoding p16 protein, refers to nucleic acid sequences which have arisen naturally in an organism, including naturally occurring mutants. The term also refers to nucleic acid sequences which, while derived from a naturally occurring p16, have been altered by mutagenesis, as for example, combinatorial mutagenesis described below, yet still encode polypeptides which have at least one activity of a p16 protein.

In one embodiment, the nucleic.acid is a cDNA encoding a peptide having at least one activity of a p16 protein. Preferably, the nucleic acid is a cDNA molecule comprising at least a portion of the nucleotide sequence encoding a p16 protein shown in SEQ ID NO: 1. A preferred portion of the cDNA molecule shown in SEQ ID NO: 1 includes the coding region of the molecule.

In another embodiment, the nucleic acid of the invention encodes a peptide having an activity of a p16 protein and comprising an amino acid sequence shown in SEQ ID NO: 2. Preferred nucleic acids encode a peptide having a p16 protein activity and being at least 60% homologous, more preferably 70% homologous and most preferably 80% homologous with an amino acid sequence shown in SEQ ID NO: 2. Nucleic acids which encode peptides having an activity of a p16 protein and having at least about 90%, more preferably at least about 95%, and most preferably at least about 98-99% homology with a sequence shown in SEQ ID NO: 2 are also within the scope of the invention. Homology refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

Another aspect of the invention provides a nucleic acid which hybridizes under high or low stringency conditions to a nucleic acid which encodes a peptide having all or a portion of an amino acid sequence shown in SEQ ID NO: 2. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids encoding peptides having p16 biological activity, as described herein, and having a sequence which differs from the nucleotide sequence shown SEQ ID NO: 1 due to degeneracy in the genetic code are also within the scope of the invention. Such nucleic acids encode functionally equivalent peptides (i.e., a peptide having a biological activity of a p16 protein) but differ in sequence from the sequence shown in SEQ ID NO: 1 due to degeneracy in the genetic code. For example, a number of amino acids are designated by more than one triplet. Codons that specify the same amino acid, or synonyms (for example, CAU and CAC are synonyms for histidine) may result in "silent" mutations which do not affect the amino acid sequence of the p16 protein. However, it is expected that DNA sequence polymorphisms that do lead to changes in the amino acid sequences of p16 proteins will exist among vertebrates. One skilled in the art will appreciate that these variations in one or more nucleotides (up to about 3-4% of the nucleotides) of the nucleic acids encoding peptides having an activity of a p16 protein may exist among individuals of a given species due to natural allelic variation. Any and all such nucleotide variations and resulting amino acid polymorphisms are within the scope of this invention.

Fragments of the nucleic acid encoding the active portion of the presently claimed p16 protein are also within the scope of the invention. As used herein, a fragment of the nucleic acid encoding the active portion of a p16 protein refers to a nucleotide sequence having fewer nucleotides than the nucleotide sequence encoding the entire amino acid sequence of a p16 protein and which encodes a peptide having an activity of a p16 protein (i.e., a peptide having at least one biological activity of a p16 protein) as defined herein. Nucleic acid fragments within the scope of the invention include those capable of hybridizing under high or low stringency conditions with nucleic acids from other species for use in screening protocols to detect p16 homologs. Nucleic acids within the scope of the invention may also contain linker sequences, modified restriction endonuclease sites and other sequences useful for molecular cloning, expression or purification of recombinant peptides having at least one biological activity of a p16 protein.

As indicated by the examples set out below, a nucleic acid encoding a peptide having an activity of a p16 protein may be obtained from mRNA present in any of a number of eukaryotic cells. It should also be possible to obtain nucleic acids encoding p16 proteins from genomic DNA obtained from both adults and embryos. For example, a gene encoding a p16 protein can be cloned from either a cDNA or a genomic library in accordance with protocols herein described, as well as those generally known to those skilled in the art. A cDNA encoding a p16 protein can be obtained by isolating total mRNA from a cell, e.g. a mammalian cell, e.g. a human cell, including tumor cells. Double stranded cDNAs can then be prepared from the total mRNA, and subsequently inserted into a suitable plasmid or bacteriophage vector using any one of a number of known techniques. The gene encoding the p16 protein can also be cloned using established polymerase chain reaction techniques in accordance with the nucleotide sequence information provided by the invention. The nucleic acid of the invention can be DNA or RNA. A preferred nucleic acid is a cDNA encoding a p16 protein having a sequence shown in SEQ ID NO: 1.

This invention also provides expression vectors containing a nucleic acid encoding a peptide having an activity of a p16 protein, operably linked to at least one regulatory sequence. Operably linked is intended to mean that the nucleotide sequence is linked to a regulatory sequence in a manner which allows expression of the nucleotide sequence. Regulatory sequences are art-recognized and are selected to direct expression of the peptide having an activity of a p16 protein. Accordingly, the term regulatory sequence includes promoters, enhancers and other expression control elements. Such regulatory sequences are described in Goeddel; *Gene Expression Technology: Methods in Enzymology* 185, Academic Press, San Diego, Calif. (1990). It should be understood that the design of the expression vector may depend on such factors as the choice of the host cell to be transformed and/or the type of protein desired to be expressed. In one embodiment, the expression vector includes a DNA encoding a peptide having an activity of a p16 protein. Such expression vectors can be used to transfect cells to thereby produce proteins or peptides, including fusion proteins or peptides encoded by nucleic acids as described herein.

Moreover, such vectors can be used as a part of a gene therapy protocol to reconstitute p16 function in a cell in which p16 is misexpressed. Examples of therapeutic vehicles for delivery of a p16 construct to a target cell are disclosed in, for example, This invention also pertains to a host cell transfected to express a polypeptide having an activity of a p16 protein. The host cell may be any prokaryotic or eukaryotic cell. For example, a p16 protein of the present invention may be expressed in bacterial cells such as *E. coli*, insect cells (baculovirus), yeast, or mammalian cells. Other suitable host cells are known to those skilled in the art.

Another aspect of the present invention concerns recombinant p16 proteins which are encoded by genes derived from eukaryotic organisms, e.g. mammals, e.g. humans, and which have at least one biological activity of a p16 protein, or which are naturally occurring dysfunctional mutants. The term "recombinant protein" refers to a protein of the present invention which is produced by recombinant DNA techniques, wherein generally DNA encoding the p16 protein is inserted into a suitable expression vector which is in turn used to transform a host cell to produce the heterologous protein. Moreover, the phrase "derived from", with respect to a recombinant gene encoding the recombinant p16, is meant to include within the meaning of "recombinant protein" those proteins having an amino acid sequence of a native p16, or an amino acid sequence similar thereto which is generated by mutations including substitutions and deletions of a naturally occurring p16 protein of a organism. Recombinant proteins preferred by the present invention, in addition to native p16 proteins, are at least 60% homologous, more preferably 70% homologous and most preferably 80% homologous with an amino acid sequence shown in SEQ ID NO: 2. Polypeptides having an activity of a p16 protein and having at least about 90%, more preferably at least about 95%, activity of a p16 protein and having at least about 90%, more preferably at least about 95%, and most preferably at least about 98-99% homology with a sequence shown in SEQ ID NO: 2 are also within the scope of the invention.

The present invention further pertains to recombinant p16 proteins which are encoded by genes derived from a organism and which have amino acid sequences evolutionarily related to a p16 protein. Such recombinant p16 proteins preferably are capable of functioning in one of either role of an agonist or antagonist of at least one biological activity of a p16. The term "evolutionarily related to", with respect to amino acid sequences of the present recombinant p16 protein, refers to p16 proteins having amino acid sequences which have arisen naturally, as well as mutational variants of p16 proteins which are derived, for example, by combinatorial mutagenesis. Recombinant proteins evolutionarily related to p16 protein preferred by the present invention are at least 60% homologous, more preferably 70% homologous and most preferably 80% homologous with an amino acid sequence shown in SEQ ID NO: 2. Polypeptides having at least about 90%, more preferably at least about 95%, and most preferably at least about 98-99% homology with a sequence shown in SEQ ID NO: 2 are also within the scope of the invention.

The present invention further pertains to methods of producing the subject p16 proteins. For example, a host cell transfected with a nucleic acid vector directing expression of a nucleotide sequence encoding the subject p16 protein can be cultured under appropriate conditions to allow expression of the peptide to occur. The peptide may be secreted and isolated from a mixture of cells and medium containing the peptide having an activity of a p16 protein. Alternatively, the peptide may be retained cytoplasmically and the cells harvested, lysed and the protein isolated. A cell culture includes host cells, media and other byproducts. Suitable media for cell culture are well known in the art. The peptide having an activity of a p16 protein can be isolated from cell culture medium, host cells, or both using techniques known in the art for purifying proteins including ion-exchange chromatography, gel filtration chromatography, ultrafiltration, electrophoresis, and immunoaffinity purification with antibodies specific for a peptide having an activity of a p16 protein. In a preferred embodiment, the p16 protein is a fusion protein containing a domain which facilitates its purification, such as a p16-GST fusion protein.

Thus, a nucleotide sequence derived from the cloning of the p16 protein of the present invention, encoding all or a selected portion of the protein, can be used to produce a recombinant form of p16 via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. insulin, interferons, human growth hormone, IL-1, IL-2, and the like. Similar procedures, or modifications thereof, can be employed to prepare recombinant p16 proteins, or portions thereof, by microbial means or tissue-culture technology in accord with the subject invention.

The recombinant p16 protein can be produced by ligating the cloned gene, or a portion thereof, into a vector suitable for expression in either prokaryotic cells, eukaryotic cells, or both. Expression vehicles for production of recombinant p16 include plasmids and other vectors. For instance, suitable vectors for the expression of p16 include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17. In some instances, it may be desirable to express the recombinant p16 by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When expression of a portion of p16 is desired, i.e. a trunction mutant, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751-757) and *Salmonella typhimurium* and its in vitro activity has been demonstrated on recombinant proteins (Miller et al. (1987) *PNAS* 84:2718-1722). Therefore, removal of an N-terminal methionine, if desired, can be achieved either in vivo by expressing p16-derived polypeptides in a host which produces MAP (e.g., *E. coli* or CM89 or *S. cerevisiae*), or in vitro by use of purified MAP (e.g., procedure of Miller et al.).

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a p16 protein. For example, the VP6 capsid protein of rotavirus can be used as an immunologic carrier protein for portions of the p16 polypeptide, either in the monomeric form or in the form of a viral particle. The nucleic acid sequences corresponding to the portion of the p16 protein to which antibodies are to be raised can be incorporated into a fusion gene construct which includes coding sequences for a late vaccinia virus structural protein to produce a set of recombinant viruses expressing fusion proteins comprising a portion of the protein p16 as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of an p16 protein and the poliovirus capsid protein can be created to enhance immunogenicity of the set of polypeptide antigens (see, for example, EP Publication No. 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can be utilized, wherein a desired portion of an p16 protein is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of the p16 proteins can also be expressed and presented by bacterial cells.

In addition to utilizing fusion proteins to enhance immunogenicity, it is widely appreciated that fusion proteins can also facilitate the expression of proteins, such as the p16 protein of the present invention. For example, as described below, the p16 protein can be generated as a glutathione-S-transferase (GST-fusion protein). Such GST fusion proteins can enable easy purification of the p16 protein, such as by the use of glutathione-derivatized matrices (see, for example, Current Protocols in Molecular Biology, eds. Ausabel et al. (N.Y.: John Wiley & Sons, 1991)). In another embodiment, a fusion gene coding for a purification leader sequence, such as a poly-(His)/enterokinase cleavage site sequence at the N-terminus of the desired portion of the p16 protein, can allow purification of the expressed p16-fusion protein by affinity chromatography using a $Ni^{2+}$ metal resin. The purification leader sequence can then be subsequently removed by treatment with enterokinase (e.g., see Hochuli et al. 1987 *J. Chromatography* 411:177; and Janknecht et al. *PNAS* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Another aspect of the invention pertains to isolated peptides having an activity of a p16 protein. A peptide having an activity of a p16 protein has at least one biological activity of a p16 protein. In preferred embodiments, a biological activity of a p16 protein includes: an ability to regulate a eukaryotic cell cycle, e.g. a mammalian cell cycle, e.g., a human cell cycle; an ability to inhibit proliferation/cell growth of a eukaryotic cell, e.g. a mammalian cell, e.g., a human cell; an ability to inhibit progression of a eukaryotic cell from G1 phase into S phase, e.g., inhibit progression of a mammalian cell from G1 phase into S phase, e.g., inhibit progression of a human cell from G1 phase into S phase; an ability to inhibit the kinase activity of a cyclin dependent kinase (cdk), e.g. a cdk active in G1 phase, e.g. cdk 4, e.g. cdk6. P16 proteins of the present invention can have biological activities which include an ability to suppress tumor growth, e.g. in a tumor cell lacking wild-type p16 or in which endogenous p16 is mis-expressed. Other biological activities of the subject p16 protein are described herein or will be reasonably apparent to those skilled in the art. A peptide having p16 bioligical activity may differ in amino acid sequence from the sequence shown in SEQ ID NO: 2 but such differences result in a modified protein which functions in the same or similar manner as a native p16 protein or which has the same or similar characteristics of a native p16 protein. Various modifications of the p16 protein to produce these and other functionally equivalent peptides are described in detail herein. The term peptide, as used herein, refers to peptides, proteins, and polypeptides.

The present invention also makes available isolated p16 protein which is isolated from, or otherwise substantially free of other extracellular proteins, especially morphogenic proteins, normally associated with the p16 protein. The term "substantially free of other extracellular proteins" (also referred to herein as "contaminating proteins") is defined as encompassing p16 preparations comprising less than 20% (by dry weight) contaminating protein, and preferably comprises less than 5% contaminating protein. Functional forms of p16 can be prepared, for the first time, as purified preparations by using a cloned gene as described herein. By "puri-fied", it is meant, when referring to a peptide or DNA or RNA sequence, that the indicated molecule is present in the substantial absence of other biological macromolecules, such as other proteins (particularly other cycle proteins such as cdk4 or cdk6, as well as other contaminating proteins). The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins) substances or solutions. The term "isolated" as also used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

Isolated peptides having the activity of a p16 protein can also be obtained by screening peptides recombinantly produced from the corresponding fragment of the nucleic acid of p16 encoding such peptides. In addition, fragments can be chemically synthesized using techniques known in the art such as conventional Merrifield solid phase f-Moc or t-Boc chemistry. For example, the p16 protein may be arbitrarily divided into fragments of desired length with no overlap of the fragments, or preferably divided into overlapping fragments of a desired length. The fragments can be produced (recombinantly or by chemical synthesis) and tested to identify those peptides having a p16 protein activity.

It is possible to modify the structure of a peptide having an activity of a p16 protein for such purposes as enhancing therapeutic or prophylactic efficacy, or stability (e.g., shelf life ex vivo and resistance to proteolytic degradation in vivo). Such modified peptides are considered functional equivalents of peptides having an activity of a p16 protein as defined herein. A modified peptide can be produced in which the amino acid sequence has been altered, such as by amino acid substitution, deletion, or addition.

Moreover, as described above, variations of the p16 peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed, Ed. by L. Stryer, WH Freeman and Co.: 1981). Whether a change in the amino acid sequence of a peptide results in a functional p16 homolog can be readily determined by assessing the ability of the variant peptide to produce a response in cells in a fashion similar to the wild-type p16. Peptides in which more than one replacement has taken place can readily be tested in the same manner.

This invention further contemplates a method of generating sets of combinatorial mutants of p16, as well as truncation mutants, and is especially useful for identifying potential variant sequences (e.g. homologs) that are functional in binding to a cdk, especially cdk4 or cdk6. The purpose of screening such combinatorial libraries is to generate, for example, novel p16 homologs which can act as either agonists or antagonist, or alternatively, possess novel activities all together. To illustrate, p16 homologs can be engineered by the present method to provide more efficient binding to cdk4, yet still retain at least a portion of an activity associated with p16. Thus, combinatorially-derived homologs can be generated to have an increased potency relative to a naturally occurring p16. Such proteins, when expressed from recombinant DNA constructs, can be used in gene therapy protocols. Likewise, mutagenesis can give rise to p16 homologs which have intracellular half-lives dramatically different than the corresponding wild-type protein. For example, the altered protein can be rendered either more stable or less stable to proteolytic degradation or other cellular process which result in destruction of, or otherwise inactivation of, a p16 protein. Such p16 homologs, and the genes which encode them, can be utilized to alter the envelope of p16 expression by modulating the half-life of the protein. For instance, a short half-life can give rise to more transient p16 biological effects and, when part of an inducible expression system, can allow tighter control of p16 levels within the cell. As above, such proteins, and particularly their recombinant nucleic acid constructs, can be used in gene therapy protocols.

In similar fashion, p16 homologs can be generated by the present combinatorial approach to act as antagonists, in that they are able to interfere with the ability of wild-type p16 to regulate cell proliferation.

In one aspect of this method, the amino acid sequences for a population of p16 homologs or other related proteins are aligned, preferably to promote the highest homology possible. Such a population of variants can include, for example, p16 homologs from one or more species, or p16 homologs from the same species but which differ due to mutation. Amino acids which appear at each position of the aligned sequences are selected to create a degenerate set of combinatorial sequences.

In a preferred embodiment, the combinatorial p16 library is produced by way of a degenerate library of genes encoding a library of polypeptides which each include at least a portion of potential p16 sequences. A mixture of synthetic oligonucleotides can be enzymatically ligated into gene sequences such that the degenerate set of potential p16 sequences are expressible as individual polypeptides, or alternatively, as a set of larger fusion proteins (e.g. for phage display) containing the set of p16 sequences therein.

There are many ways by which the library of potential p16 homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential p16 sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of p16 homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate p16 sequences created by combinatorial mutagenesis techniques.

In yet another screening assay, the candidate p16 gene products are displayed on the surface of a cell or viral particle, and the ability of particular cells or viral particles to bind a cdk, such as cdk4 or cdk6, via this gene product is detected in a "panning assay". For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). In a similar fashion, fluorescently labeled molecules which bind p16 can be used to score for potentially functional p16 homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E.coli* filamentous phages M13, fd, and f1 are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007-16010; Griffths et al. (1993) *EMBO J* 12:725-734; Clackson et al. (1991) *Nature* 352:624-628; and Barbas et al. (1992) *PNAS* 89:4457-4461).

In an illustrative embodiment, the recombinant phage antibody system (RPAS, Pharmacia Catalog number 27-9400-01) can be easily modified for use in expressing and screening p16 combinatorial libraries. For instance, the pCANTAB 5 phagemid of the RPAS kit contains the gene which encodes the phage gIII coat protein. The p16 combinatorial gene library can be cloned into the phagemid adjacent to the gIII signal sequence such that it will be expressed as a gIII fusion protein. After ligation, the phagemid is used to transform competent *E. coli* TG1 cells. Transformed cells are subsequently infected with M13KO7 helper phage to rescue the phagemid and its candidate p16 gene insert. The resulting recombinant phage contain phagemid DNA encoding a specific candidate p16, and display one or more copies of the corresponding fusion coat protein. The phage-displayed candidate p16 which are capable of binding a cdk are selected or enriched by panning. For instance, the phage library can be panned on glutathione immobilized cdk4-GST fusion proteins, and unbound phage washed away from the cells. The bound phage is then isolated, and if the recombinant phage express at least one copy of the wild type gIII coat protein, they will retain their ability to infect *E. coli*. Thus, successive rounds of reinfection of *E. coli*, and panning will greatly enrich for p16 homologs, which can then be screened for further biological activities in order to differentiate agonists and antagonists.

In light of the present disclosue, other forms of mutagenesis generally applicable will be apparent to those skilled in the art in addition to the aforementioned rationale mutagenesis based on conserved versus non-conserved residues. For example, p16 homologs (both agonist and antagonist forms) can be generated and screened using, for example, alanine scanning mutagenesis and the like (Ruf et al. (1994) *Biochemistry* 33:1565-1572; Wang et al. (1994) *J Biol Chem* 269:3095-3099; Balint et al. (1993) *Gene* 137:109-118; Grodberg et al. (1993) *Eur J Biochem* 218:597-601; Nagashima et al. (1993) *J Biol Chem* 268:2888-2892; Lowman et al. (1991) *Biochemistry* 30:10832-10838; and Cunningham et al. (1989) *Science* 244:1081-1085), by linker scanning mutagenesis (Gustin et al. (1993) *Virology* 193:653-660; Brown et al. (1992) *Mol Cell Biol* 12:2644-2652; McKnight et al. (1982) *Science* 232:316); or by saturation mutagenesis (Meyers et al. (1986) *Science* 232:613).

Another aspect of the invention pertains to an antibody specifically reactive with a peptide having an activity of a p16 protein. For example, by using peptides having an activity of a p16 protein based on the cDNA sequence of a p16 protein, anti-protein/anti-peptide antisera or monoclonal antibodies can be made using standard methods. A mammal such as a mouse, a hamster or rabbit can be immunized with an immunogenic form of the peptide (e.g., p16 protein or an antigenic fragment which is capable of eliciting an antibody response). Techniques for conferring immunogenicity on a protein or peptide include conjugation to carriers or other techniques well known in the art. A peptide having an activity of a p16 protein can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-p16 antisera can be obtained and, if desired, polyclonal anti-p16 antibodies isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495-497), as the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with a p16 protein and the monoclonal antibodies isolated.

The term antibody as used herein is intended to include fragments thereof which are also specifically reactive with a p16 protein. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-p16 portion.

Both monoclonal and polyclonal antibodies (Ab) directed against p16 or p16 variants, and antibody fragments such as Fab' and $F(ab')_2$, can be used to block the action of p16 and allow the study of the cell cycle or cell proliferation.

Antibodies which specifically bind p16 epitopes can also be used in immunohistochemical staining of tissue samples in order to evaluate the abundance and pattern of expression of p16. Anti-p16 antibodies can be used diagnostically in immuno-precipitation and immuno-blotting to detect and evaluate p16 levels in tissue or bodily fluid as part of a clinical testing procedure. For instance, such measurements can be useful in predictive valuations of the onset or progression of tumors. Likewise, the ability to monitor p16 levels in an individual can allow determination of the efficacy of a given treatment regimen for an individual afflicted with such a disorder. The level of p16 can be measured in bodily fluid, such as in samples of cerebral spinal fluid, or can be measured in tissue, such as produced by biopsy. Diagnostic assays using anti-p16 antibodies can include, for example, immunoassays designed to aid in early diagnosis of a neoplastic or hyperplastic disorder, e.g. the presence of cancerous cells in the sample, e.g. to detect cells in which a lesion of the p16 gene has occurred.

For example, the present method provides a method for determining if a subject is at risk for a disorder characterized by unwanted cell proliferation. In preferred embodiments, method can be generally characterized as comprising detecting, in a tissue of said subject, the presence or absence of a genetic lesion characterized by at least one of (i) a mutation of a gene encoding p16 or (ii) the mis-expression of the p16 gene. To illustrate, such genetic lesions can be detected by ascertaining the existence of at least one of (i) a deletion of one or more nucleotides from the p16 gene, (ii) an addition of one or more nucleotides to the p16 gene, (iii) a substitution of one or more nucleotides of the p16 gene, (iv) a gross chromosomal rearrangement of the p16 gene, (v) a gross alteration in the level of a messanger RNA transcript of the p16 gene, (vi) the presence of a non-wild type splicing pattern of a messanger RNA transcript of the p16 gene, and (vii) a non-wild type level of the p16 protein. In one aspect of the invention there is provided probe/primer comprising an oligonucleotide containing a region of nucleotide sequence which is capable of hybridizing to a sense or antisense sequence of SEQ ID No. 1 or naturally occuring mutants thereof, or 5' or 3' flanking sequences or intronic sequences naturally associated with the p16 gene. The probe is exposed to nucleic acid of a tissue sample; and the hybridization of the probe to the sample nucleic acid is detected. In certain embodiments, detection of the lesion comprises utilizing the probe/primer in a polymerase chain reaction (PCR), or, alternatively, in a ligation chain reaction (LCR), the later of which can be particularly useful for detecting even point mutations in the p16 gene. Alternatively, the level of p16 protein can detected in an immunoassay.

Another application of anti-p16 antibodies is in the immunological screening of cDNA libraries constructed in expression vectors such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of p16 can then be detected with antibodies, as, for example, reacting nitrocellulose filters lifted from infected plates with anti-p16 antibodies. Phage, scored by this assay, can then be isolated from the infected plate. Thus, the presence of p16 homologs can be detected and cloned from other sources.

The nucleotide sequence determined from the cloning of p16 from a human cell line will further allow for the generation of probes designed for use in identifying p16 homologs in other human cell types, particularly cancer or other transformed or immortalized cells, as well as p16 homologs from other animals.

In addition, nucleotide probes can be generated from the cloned sequence of the p16 protein, which allow for histological screening of intact tissue and tissue samples for the presence of p16 mRNA. Similar to the diagnostic uses of anti-p16 antibodies, the use of probes directed to p16 mRNA, or to genomic p16 sequences, can be used for both predictive and therapeutic evaluation of allelic mutations which might be manifest in, for example, neoplastic or hyperplastic disorders (e.g. unwanted cell growth). Used in conjunction with anti-p16 antibody immunoassays, the nucleotide probes can help facilitate the determination of the molecular basis for a developmental disorder which may involve some abnormality associated with expression (or lack thereof) of a p16 protein. For instance, variation in p16 synthesis can be differentiated from a mutation in the p16 coding sequence.

Also, the use of anti-sense techniques (e.g. microinjection of antisense molecules, or transfection with plasmids whose transcripts are anti-sense with regard to p16 mRNA) can be used to investigate role of p16 in the cell cycle and cell proliferation, in a controlled p16 environment, by inhibiting endogenous p16 production. Such techniques can be utilized in cell culture, but can also be used in the creation of transgenic animals.

The present invention, by making available purified and recombinant p16 protein, will allow the development of assays which can be used to screen for drugs which are either agonists or antagonists. By mutagenesis, and other structural surveys of the p16 protein family, rationale drug design can be employed to manipulate p16 or portions thereof, as either agonists or antagonists, as well as facilitate design of small molecule agonists and antagonists. By employing, for example, scanning mutagenesis to map the residues of p16 involved in cdk4 and cdk6 interaction, peptidomimetic compounds, e.g. diazepine (benzodiazepine) or isoquinoline derivatives, can be generated which are capable of binding cdk4 or cdk6 (without interfering with their ability to bind cyclins and other cell cycle proteins, yet prevent p16 from binding and inactivating cdk4. More preferable, however, are peptidomimetics which, like the p16 sequence from which they may derive, bind and inactivate a cdk, e.g. cdk4, e.g. cdk6, and can thereby provide agents which are more easily administered, e.g. systemic, and which are able to cross the cell membrane and become localized in the cell.

In another aspect, the invention features transgenic non-human animals which express a p16 gene of the present invention, or which have had their p16 gene(s), e.g. heterozygous or homozygous, disrupted in at least one of the tissue or cell-types of the animal.

In another aspect, the invention features an animal model for developmental diseases, which has a p16 allele which is mis-expressed. For example, a mouse can be bred which has a p16 allele deleted, or in which all or part of one or more p16 exons are deleted. Such a mouse model can then be used to study disorders arising from mis-expressed p16 genes.

I. Cyclin/cdk Complexes in Normal Cells

As described previously (see U.S. patent applications Ser. Nos. 08/154,915, 07/991,997 and 07/963,308, as well as Xiong et al. (1993) *Nature* 366:701; Xiong et al. (1993) *Genes Dev* 7:1572; Xiong et al. (1992) *Cell* 71:505; and Zhang et al. (1993) *Mol Cell Biol* 4:897), immunological procedures have been used to establish that cyclins associate, in eukaryotic cells, with a variety of potential catalytic subunits (e.g., CDKs, such as CDK2, cdk4 and CDK5). In addition, these procedures have shown that, in untransformed cells, cyclin/CDK complexes can further associate with the replication factor PCNA and a polypeptide of 21 kDa apparent molecular weight.

To illustrate, human cyclin D1 has been associated with a wide variety of proliferative diseases. As described, in human diploid cells, specifically human diploid fibroblasts, cyclin D1 is complexed with a number of other cellular proteins. Among them are the catalytic subunits CDK2, cdk4 (previously called PSK-J3), and CDK5 (also called PSSALRE). In addition, polypeptides of 21 kDa and 36 kDa were identified in association with cyclin D1. It was shown that the 36 kDa protein is the Proliferating Cell Nuclear Antigen, PCNA. PCNA has been described as an essential accessory factor to the delta polymerase, which is required for leading-strand DNA replication and DNA repair. Cyclin D3 was also found to associate with multiple protein kinases, p21 and PCNA. It was therefore proposed that there exists a quaternary complex of D type cyclins, CDK, PCNA and p21, and that many combinatorial variations (cyclin D1, D3 with CDK2, 4 and 5) may assemble in vivo. Moreover, it was demonstrated that pSK-J3/cdk4 is the predominant cyclin dependent kinase (cdk) associated with Cyclin D1.

II. Cyclin/cdk Complexes in Transformed Cells

The importance of the quaternary complex is emphasized by the discovery that cellular transformation by DNA tumor viruses is associated with selective subunit rearrangement of the cyclin D complexes, as well as other cell-cycle complexes, including cyclin A, CDC2, CDK2, cdk4 and CDK5 complexes. In particular, introduction of SV40 DNA tumor virus or its oncogenic gene product large T antigen into normal human diploid fibroblasts (HDF) causes disruption of the association between cyclin D and PCNA, CDKs (such as CDK2, cdk4 and CDK5) and p21. For example, as described herein (and previously in U.S. patent application Ser. Nos. 08/154,915 and 07/991,997), after dissociation from cyclin D and p21, cdk4 kinase becomes associated with a 16 kDa polypeptide (p16). Similarly, SV40 transformation causes a decrease of association of p21 with cyclin A in HDF; and adenovirus-(293 cell line) or human papilloma virus-(HeLa cell line) transformed cells, p21 is completely disassociated from cyclin A. A 19 kDa peptide, p19, then appears in a complex with cyclin A. Therefore, p21 is associated with cyclin kinases only in normal, untransformed cells, whereas p16, p19 and possibly other related proteins are present in cyclin complexes in transformed cells.

Thus, striking evidence is provided that the cyclin/CDK family of enzymes that act at multiple key steps in the cell division are grossly altered in a variety of oncogenically transformed cells. For example, in transformed cells, cdk4 totally dissociates from cyclin D, PCNA, and p21 and, instead, associate exclusively with a polypeptide of 16 kd (p16). This pattern of subunit rearrangement of cyclin-CDK complexes has been discovered not only in SV40-transformed cells, but also in cells transformed with adenovirus or papilloma virus. Moreover, the pattern of subunit composition of the cyclin-CDK family was grossly abnormal in non-virally transformed cells.

In many transformed cells, cyclin and CDK's associate in binary complexes which form the core of the cell cycle regulatory machinery. In normal cells, a major fraction of the cyclin kinases acquire two additional subunits and thereby form quaternary complexes. Reconstitution of quaternary complexes in insect cells revealed that p21 is a universal inhibitor of cyclin kinases. As such, p21 inhibits cell cycle progression and cell proliferation upon overexpression in mammalian cells. Taken in conjunction with the previously demonstrated absence of p21 protein in the cell cycle kinase complexes of cells with deficient p53, these results suggest that p21 could be a transcriptional target of the tumor suppressor protein, p53. One function of p53 is to act in a cellular signaling pathway which causes cell cycle arrest following DNA damage (see for example, Kastan et al. Cell 71:587-5971993). It is therefore presently suggested that p21 forms a critical link between p53 and the cell cycle control machinery.

III Role of p16 in Cell-Cycle Regulation

Deregulation of cell proliferation is a hallmark of neoplastic transformation. Alteration in growth control pathways must translate into changes in the cell cycle regulatory machinery, but the mechanism by which this occurs is largely unknown. As described above, compared to normal human fibroblasts, cells transformed with a variety of viral oncoproteins show striking changes in the subunit composition of the cyclin dependent kinases . In normal cells, CDKs exist predominantly in multiple quaternary complexes, each containing a CDK, cyclin, PCNA and p21. However, in many transformed cells PCNA and p21 are lost from these multiprotein enzymes.

Cyclin D/cdk4 kinase differs from the others in its inability to utilize histone H1 as a substrate. To date, the only substrates known for cyclin D/cdk4 kinases are the members of the RB family of "pocket" proteins (Matsushime et al., Cell 71:323-334 (1992)). Therefore, the effect of p21 was tested on the ability of cyclin D/cdk4 to phosphorylated RB. Insect cell lysates containing cyclin D or cdk4 alone showed little activity toward GST-RB. However, cyclin D/cdk4 binary complexes catalyzed substantial RB phosphorylation. Addition of increasing amounts of p21 resulted in the accumulation of cyclin D/cdk4/p21 ternary complexes with a corresponding inhibition of RB phosphorylation. Again, inclusion of PCNA was essentially without effect.

A. Cloning of p16, and Inhibitor of cdk4

The two-hybrid screening system (Fields et al. Nature 340: 254 (1989)) was utilized to search for proteins that could interact with human cdk4, and more specifically, to isolate a cDNA encoding p16. Two-hybrid screening relies on reconstituting a functional GAL4 activator from two separated fusion proteins: the GAL4 DNA-binding domain fused to cdk4, GAL4db-cdk4; and the GAL4 activation domain fused to the proteins encoded by HeLa cDNAs, GAL4ad-cDNA. YPB2 was used as the recipient yeast as it is a strain that contains two chromosomal genes under the control of two different GAL4-dependent promoters: HIS3and LacZ. YPB2 was transformed with a mixture of two plasmids encoding, respectively, the GAL4db-cdk4 and the GAL4ad-cDNA fusions; several clones were obtained that grew in the absence of histidine and that turned blue in the presence of β-gal. From DNA sequencing data it was determined that each of the positive clones derived from the same gene, although one group represented mRNAs with a shorter 3' end. The sequence of these cDNAs contained, in-phase with the GAL4ad, an open reading frame encoding a protein of 148 amino acids with a predicted molecular weight of 15,845 daltons (see SEQ ID Nos. 1 and 2). This protein is referred to hereinafter as INK4 (inhibitor of cdk4; see below). The sequence of p16INK4 was compared by standard methods with those present in the currently available data banks and no significant homologies were found.

To test if p16INK4 would specifically bind cdk4, YPB2 were cotransformed with the GAL4ad-p16INK4 fusion as well as with several target GAL4db fusion constructs containing, respectively, cdc2, CDK2, cdk4, CDK5, PCNA and Snfl (a fission yeast kinase). Transformed cells were plated with and without histidine. Only the GAL4db-cdk4 fusion interacted with GAL4ad-p16INK4 to an extent which allowed growth in the absence of histidine, indicating that this pair of fusion proteins specifically reconstituted a functional GAL4 activator able to enhance the expression of the HIS3 gene. The same result was obtained when the ability to transactivate the expression of the β-galactosidase gene was assayed.

The specificity of this interaction was further demonstrated in a cell-free system, by mixing in vitro translated ($^{35}$S)-labeled CDKs with a purified bacterially-produced fusion protein consisting of glutathione-S transferase (GST) linked to p16INK4 (17). The GST-p16INK4 fusion was recovered by binding to glutathione-sepharose beads and the association of each CDK was analyzed by gel electrophoresis. Consistent with the previous observations, GST-p16INK4 bound much more efficiently to cdk4 than to cdc2, CDK2 or CDK5.

Since the predicted molecular weight of p16INK4 is close to 16 Kd, the identity of p16INK4 as the cdk4-associated p16 protein found in transformed cell lines (see above) was determined. Two in vitro translation products of 15 KD and 17 KD were obtained from the p16INK4 cDNA. These products, as well as the cdk4-associated p16 protein from HeLa cells were treated with N-chlorosuccinimide. The partial NCS-proteolytic pattern of the 17 KD cDNAINK4-derived product was very similar to the pattern obtained with the cdk4-associated p16 protein from HeLa cells, strongly suggesting that the p16INK4 cDNA actually corresponds to p16. Partial digestion with V8 protease of the 17 KD cDNAINK4-derived product and p16 also yielded similar patterns. It is interesting to note that the p16INK4 protein overexpressed in insect cells has an electrophoretic mobility of 15 KD, and its NCS proteolytic map is identical to that obtained with the 15 KD cDNA derived product. This suggests that the actual p16INK4 found in human cells and the 17 KD in vitro translation product correspond to posttranslationally modified proteins. The fact that the p16INK4protein overexpressed in insect cells interacts with cdk4 suggests that this modification is not essential for the interaction (see below).

The identity between p16INK4 and the cdk4-associated protein p16 was further confirmed using antibodies raised against the purified GST-p16INK4 fusion protein. Several human cell lines were used for this experiment: a normal cell line WI38, derived from normal lung fibroblasts; the VA13 cell line derived from WI38 by transformation with the SV40 T-antigen; and HeLa cells. As set out above, anti-cdk4 immunoprecipitates of WI38 revealed the association of cdk4 with cyclin D1, PCNA, p21 and p16. In contrast, in VA13 and HeLa cells cdk4 is only associated with p16. Anti-p16INK4 immunoprecipitates contained a protein with an apparent molecular weight of 16 KD which was readily detectable in the two transformed cell lines, VA13 and HeLa but to a lesser extent in the normal cell line WI38. This protein not only had the same electrophoretic mobility as the p16 protein coimmunoprecipitated with anti-cdk4 serum, but also had an identical NCS partial proteolytic pattern. In addition to p16INK4 a protein of 33 Kd was observed in anti-p16 coimmunoprecipitates that was shown to be identical to cdk4 by V8-proteolytic mapping.

Northern analysis of the transcripts present in WI38 and VA13 cells indicated that the p16INK4 mRNA was around many times less abundant in WI38 cells compared to VA13 cells. This difference approximately corresponded to the observed difference in the amount of p16 protein between the two cell lines, suggesting the possibility that p16INK4 expression might be regulated at a transcriptional or post-transcriptional level. Indeed, in three non-virally transformed cell lines the expression of p16INK4 could not be detected even after overexposure of the gel.

To study the biochemical consequences of the interaction of p16INK4 with cdk4, active cdk4-cyclin D complexes have been reconstituted in vitro by standard protocols (Kato et al. *Genes Der* 7:331 (1993); and Ewen et al. *Cell* 73:487 (1993)). The three relevant components, cdk4, p16INK4 and cyclin D1, were expressed in baculovirus-infected insect cells. Extracts were prepared from metabolically ($^{35}$S)-labeled insect cells that separately overexpressed p16INK4, cdk4 or cyclin D1, as well as from cells overexpressing both cdk4 and cyclin D1. In response to increasing amounts of p16INK4, corresponding decreases in the ability of cdk4 to phosphorylate Rb was observed. This inhibition correlated with the association between p16INK4 and cdk4 as detected by immunoprecipitation. No inhibition was observed when CDK2-cyclin D2 complexes were used in a similar assay. To confirm that the inhibition of cdk4 was due to p16INK4, a His-tagged p16INK4 fusion protein (His-p16INK4) was created to have an amino terminal extension of 20 amino acids containing a tract of 6 histidine residues. This fusion protein was overexpressed in baculovirus-infected insect cells, and was purified by virtue of the high-affinity association of the histidine tract to nickel-agarose beads. The His-p16INK4 protein preparation was shown to be >90% pure, and inhibited the activity of the cdk4-cyclin D1 complex under conditions similar to those used for inhibition by the whole lysates.

The role of the retinoblastoma gene product (Rb), appears to be as a cell cycle checkpoint which appears to at least act be sequestering transcription factors responsible for the proteins of S phase. In many carcinomas, p53 function is lost by mutation or deletion. Rb, on the other hand, is not apparently altered as often. However, because p16 down-regulates the cdk4/cyclin D complex, which acts to phosphorylate Rb, it is proposed herein that p16 loss in certain carcinomas can alleviate the effects of the Rb checkpoint and, in some manner of speaking, represent a checkpoint deficiency analogous to p53 loss. The loss of p16 would result in more effective phosphorylation of Rb and hence would remove the Rb-mediated inhibition of the cell cycle. Consistent with this notion, it is described below that in a variety of human tumor cells, such as cells which over-express a D-type cyclin, e.g. cyclin D1 or D2, the p16 gene is lost from the cell, e.g. homozygously deleted.

Moreover, as described in the examples below, the p16 gene was found to map to the human region 9p21-22, a known melanoma locus (Walker et al. (1994) *Oncogene* 9:819; Coleman et al. (1994) *Cancer Res* 54:344; Cheng et al. (1993) *Cancer Res* 53:4761; and Cannon-Albright et al. (1992) *Science* 258:1148). The chromosomal mapping was further confirmed by analysis of somatic cell hybrids through PCR amplification (using primers ex1A and ex13 of FIG. 2A). Somatic hybrids containing human chromosome 9 resulted in positive PCR products being appified.

Utilizing primers generated from the cDNA sequence of human p16 (SEQ ID No. 1) which are shown in FIG. 1, the genomic p16 gene was partially sequenced to determine intron/exon boundaries. The approximate sequences of the nucleic acid flanking Exon 1 and Exon 2 (see FIG. 1) are shown in FIGS. 2A and 2B and 3A-3C (SEQ ID Nos: 11-15), respectively.

Genomic DNA was isolated from a variety of human tumor lines (Sambrook et al. *Molecular Cloning: A Laboratory Manual*, CSHL Press, Cold Spring Harbor, N.Y. (1989)) and was probed by PCR reactions for the presence or absence of p16 sequences. In particular, primers ex1A and ex13 (FIG. 2A); residues 342-359 of SEQ ID No. 3 and 72-95 of SEQ ID No. 5 were used to score for exon 1 of p16, and primers ex14 and ex15 were likewise used to detect exon 2 of p16. As shown in FIG. 4, the p16 gene is disrupted in several tumor cell lines, confirming that p16 is indeed likely to be critical in cell transformation in certain cancerous cells. Moreover, probing of these cell lines with full length p16 cDNA (SEQ ID No. 1) demonstrated that in at least 3 of those cells apparently missing a portion of the p16 gene, the entire gene was in fact absent.

The present invention will now be illustrated by the following examples, which are not intended to be limiting in any way.

EXAMPLE 1

Demonstration of Selective Subunit Rearrangement of Cell Cycle Complexes In Association With Cellular Transformation by a DNA Tumor Virus or Its Oncogenic Product (i) Cellular Transformation With DNA Tumor Virus SV40 is Associated With Subunits Rearrangement of Cell Cycle Complexes Preparation of [$^{35}$S] methionine-labelled cell lysates and polyacrylamide gel electrophoresis were as described above, as well as described in PCT Publication No. WO92/20796. Cell lysates were prepared from either human normal diploid fibroblast cells WI38 or DNA tumor virus SV40 transformed WI38 cells, VA13. Cell lysates were immunoprecipitated with antibodies against each cell cycle gene products.

(ii) Subunit Rearrangements of Cell Cycle Complexes in Two Different Pair Cell Lines Methods for preparation of cell lysates are the same as described above. Two different pair cell lines were used in these experiments. HSF43 is a normal human diploid fibroblast cell line and CT10 (full name CT10-2C-T1) is a derivative of HSF43 transformed by SV40 large tumor antigen. CV-1 is an African green monkey kidney cell line and COS-1 is a derivative of CV-1 transformed by SV40.

(iii) Cellular Transformation by DNA Tumor Virus SV40 is Associated With Rearrangement of PCNA Subunit of Cell Cycle Complexes Preparation of cell lysate, electrophoresis, and Western blotting conditions are the same as described above. Normal human diploid fibroblast cell lines and their SV40 transformed cell lines are described above. Immrunoprecipitates derived from each antibody were separated on polyacrylamide gels and blotted with anti-PCNA antibody.

(iv) Cellular Transformation by DNA Tumor Virus SV40 is Associated With Rearrangement of cdk4 Subunit of Cell Cycle Complexes Preparation of cell lysate, electrophoresis, and Western blotting conditions are the same as previously described. Normal human diploid fibroblast cell lines and their SV40 transformed cell lines are described above. Immunoprecipitates derived from each antibody were separated on polyacrylamide gels and blotted with anti-cdk4 antibody.

EXAMPLE 2

Cloning of $p16^{INK4}$, An Inhibitor of cdk4 Activity (i) Cloning of $p16_{INK4}$ Using the Two Hybrid Assay

*Saccharomyces cerevisiae* YPB2 cells were transformed simultaneously with a plasmid containing a GAL4db-p16INK4 fusion and with a plasmid containing, respectively, the GAL4ad fused to cdc2 (CDK1), CDK2, cdk4, CDK5, PCNA (proliferating cell nuclear antigen), and the fission yeast kinase Snf 1. After growing cells in medium selective for both plasmids (minus tryptophan and minus leucine), two colonies were picked randomly and were streaked in plates that either contained or lacked histidine. The ability to grow in the absence of histidine depends on the expression of the HIS3 gene that is under a GAL4-responsive promoter and, therefore, indicates that a functional GAL4 activator has been reconstituted through the interaction of p16INK4 with the corresponding target protein.

(ii) Interaction of $p16^{INK4}$ CDKs

Purified bacterially-produced GSTp16INK4 fusion protein was mixed with ($^{35}$S)-labeled in vitro translated cdc2, CDK2, cdk4 and CDK5. Mixtures contained 0.5 μg of purified GST-p16INK4 and an equivalent amount of in vitro translated protein (between 0.5 to 5, μl; TNT Promega) in a final volume of 200 μl of a buffer containing 50 mM Tris-HCl pH 8, 120 mM NaCl and 0.5% Nonidet P-40. After 1 h at 4° C., 15 μl of glutathione-agarose beads were added and incubation was resumed for an additional hour. Beads were recovered by centrifugation, washed 4 times with the incubation buffer, and mixed with standard protein-gel loading buffer. Samples were loaded into a 15% poly-acryllamide gel and ($^{35}$S)-labeled proteins were detected by fluorography. The GSTp16INK4 fusion protein was overexpressed in the pGEX-KG vector and purified by standard techniques. The in vitro translation templates were derived from the pBluescript vector (Stratagene).

(iii) Proteolytic Mapping of $p16^{INK4}$

The in vitro translated ($^{35}$S)-labeled p16INK4 (TNT Promega) was obtained using the p16INK4 cDNA cloned into pBluescript vector (Stratagene) as a template, and the cdk4-associated p16 protein was co-immunoprecipitated with an anti-cdk4 serum from metabolically ($^{35}$S)-labeled HeLa cells lysates. Partial proteolysis was done over the corresponding gel slices after extensive equilibration in a buffer and digestion was accomplished by addition of NCS at different concentrations. The products were run in a 17.5% polyacrilamide gel and detected in a phosphoimager Fujix 2000.

(iv) Detecting the Effects of $p16^{INK4}$ on cdk4-Cyclin D Complexes

Baculovirus-infected insect cells overexpressing p16INK4, cdk4, cyclin D1, or both cdk4 and cyclin D1 together were metabolically ($^{35}$S)-labeled. The different incubation mixtures were composed by extracts containing p16INK4, cdk4, cyclin D1 and both cdk4 and cyclin D1, and were immunoprecipitated with anti-p16INK4 serum, anti-cdk4 serum without any previous preincubation, and anti-CDK serum preincubated with the peptide originally used to raise the antiserum and anti-cyclin D1 serum. Immunoprecipitates were then analyzed by SDS-PAGE.

EXAMPLE 3

Chromosomal Mapping of $p16^{INK4}$

Genomic clones of the human p16 gene were isolated by stringency screening (68° C. With 0.1×SSC wash) of a λFIXII human genomic library (Strategene) with cDNA probes. Isolated phage clones were confirmed by high stringency Southern hybridization and/or partial sequence analysis. Purified whole phage DNA was labelled for fluorescent in situ hybridization (FISH) analysis.

FISH analysis was performed using established methods (Demetrick et al. (1994) *Cytogenet Cell Genet* 66:72-74; Demetrick et al. (1993) *Genomics* 18:144-147; and DeMarini et al. (1991) *Environ Mol Mutagen* 18:222-223) on methotrexate or thymidine synchronized, phytohemagglutinin stimulated, normal peripheral blood lymphocytes. Suppression with a mixture of sonicated human DNA and cot1 DNA was required to reduce the background. The stained slides were counterstained with propidiem iodide (for an R banding pattern) or DAPI and actinomycin D (for a DA-DAPI banding pattern), mounted in antifade medium and visualized utilizing a Zeiss Axiphot microscope. Between 30 and 100 mitotises were examined for each gene location. Photographs were taken using a cooled CCD camera. Alignment of three color fluorescence was done under direct visualization through a triple bandpass filter (FITC/Texas Red/DAPI). The p16 gene was visualized to map to 9p21-22.

EXAMPLE 4

Generation of Transgenic Mice Having Disrupted a $p16^{INK4}$ Gene

We have isolated a λ genomic clone containing the coding region for the mouse p16 gene. This DNA (14 kB) has been cloned in two independent pieces and the restriction map for nine restriction endonucleases has been performed (see FIG. 5). The mouse gene p16 has been completely sequenced and the coding region is apparently made up of only two exons that have been located in the restriction map by Southern hybridization.

The disruptive construct is formed by the two DNA regions of approx. 3-4 Kb flanking the p16 gene. These DNA pieces are cloned at both sides of a gene marker that will be used to select the mouse cells that have incorporated this DNA. Those cells where insertion has occurred in the appropriate position are injected into mouse vlastocytes and implanted into the appropriate female mice following standard protocols (*Manipulating the Mouse Embryo*, (Cold Spring Harbor Laboratory Press, Cold Spring Harbor, N.Y., 1986; and Jaenisch (1988) *Science* 240:1468-1474.)

All of the above-cited references and publications are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated polypeptide comprising a p16$^{INK4}$ amino acid sequence encoded by a nucleic acid which hybridizes under stringency conditions of 6.0×sodium chloride/sodium citrate at about 45° C., followed by a wash of 2.0×SSC at 50° C. to the nucleic acid sequence set forth in SEQ ID NO: 1, which p16$^{INK4}$ amino acid sequence specifically binds a cyclin dependent kinase (cdk).

2. The polypeptide of claim 1, comprising the amino acid sequence designated in SEQ ID NO: 2.

3. The polypeptide of claim 1, which polypeptide is a mammalian p16$^{INK4}$ polypeptide.

4. The polypeptide of claim 1, which polypeptide is a human P16$^{INK4}$ polypeptide.

5. The polypeptide of claim 1, which polypeptide is the purified product of recombinant protein expression.

6. The polypeptide of claim 1, wherein said polypeptide comprises at least 50 contiguous amino acid residues of SEQ ID NO: 2, which polypeptide binds to a cdk.

7. The polypeptide of any of claims 2, 3 or 4, which polypeptide is substantially free of other extracellular proteins.

8. The polypeptide of claim 1, wherein the cdk is cdk4 or cdk6.

9. The polypeptide of claim 8, which polypeptide inhibits a kinase activity associated with said cdk.

10. The polypeptide of claim 9, wherein said polypeptide is a fusion protein that is functional in a two-hybrid assay.

11. The polypeptide of claim 10, wherein said fusion protein comprises glutathione-S-transferase polypeptide.

12. The polypeptide of claim 8, wherein said cdk is a human cdk.

13. The polypeptide of claim 1, wherein said polypeptide has a molecular weight of about 16 kD.

14. The polypeptide of claim 1, which polypeptide is substantially free of other extracellular proteins.

15. The polypeptide of claim 1, which polypeptide is the product of recombinant protein expression.

16. The polypeptide of claim 1, wherein said polypeptide is encoded by a nucleic acid which includes the coding sequence designated by SEQ ID NO: 1.

17. An isolated polypeptide encoded by a nucleic acid which encodes a p16$^{INK4}$ amino acid sequence encoded by a nucleic acid molecule which hybridizes under stringency conditions of 6.0×sodium chloride/sodium citrate at about 45° C., followed by a wash of 2.0×SSC at 50° C. to the nucleic acid sequence set forth in SEQ ID NO: 1, which p16$^{INK4}$ amino acid sequence specifically binds a cyclin dependent kinase (cdk).

* * * * *

SEQUENCE LISTING

<160> NUMBER OF SEQ ID NOS: 15

<210> SEQ ID NO 1
<211> LENGTH: 957
<212> TYPE: DNA
<213> ORGANISM: Homo sapiens

<400> SEQUENCE: 1

```
cggagaggga attcggcacg aggcagcatg gagccttcgg ctgactggct ggccacggcc      60
gcggcccggg gtcgggtaga ggaggtgcgg gcgctgctgg aggcggtggc gctgcccaac     120
gcaccgaata gttacggtcg gaggccgatc caggtcatgg atgatgggca gcgccccgag     180
tggcggagct gctgctgctc cacggcgcgg agcccaactc gcccgacccc gccactctca     240
cccgacccgt gcaccacgct gcccgggagg gcttctggac acgctggtgg tgctgcaccg     300
ggccggggcg cggctggacg tgcgcgatgc ctggggccgt ctgcccgtgg acctggctga     360
ggagctgggc catcgcgatg tcgcacggta cctgcgcgcc cgtgcggggg gcaccagagg     420
cagtaaccat gcccgcatag atgccgcgga aggtccctca gacatccccg attgaaagaa     480
ccagagaggc tctgagaaac ctcgggaaac ttagatcatc agtcaccgaa ggtcctacag     540
ggccacaact gcccccgcca caacccaccc cgctttcgta gttttcattt agaaaataga     600
gcttttaaaa atgtcctgcc ttttaacgta gatataagcc ttcccccact accgtaaatg     660
tccatttata tcattttta tatattctta taaaaatgta aaaaagaaaa caccgcttct     720
gccttttcac tgtgttggag ttttctggag tgagcactca cgccctaagc gcacattcat     780
gtgggcattt cttgcgagcc tcgcagcctc cggaagctgt cgacttcatg acaagcattt     840
tgtgaactag ggaagctcag gggggttact ggcttctctt gagtcacact gctagcaaat     900
ggcagaacca aagctcaaat aaaaataaaa ttattttcat tcattcactc aaaaaaa      957
```

<210> SEQ ID NO 2
<211> LENGTH: 148
<212> TYPE: PRT
<213> ORGANISM: Homo sapiens

<400> SEQUENCE: 2

```
Met Glu Pro Ser Ala Asp Trp Leu Ala Thr Ala Ala Arg Gly Arg
1               5                   10                  15

Val Glu Glu Val Arg Ala Leu Leu Glu Ala Val Ala Leu Pro Asn Ala
                20                  25                  30

Pro Asn Ser Tyr Gly Arg Arg Pro Ile Gln Val Met Met Met Gly Ser
            35                  40                  45

Ala Arg Val Ala Glu Leu Leu Leu Leu His Gly Ala Glu Pro Asn Cys
    50                  55                  60

Ala Asp Pro Ala Thr Leu Thr Arg Pro Val His Asp Ala Ala Arg Glu
```

```
                65                  70                  75                  80
Gly Phe Leu Asp Thr Leu Val Val Leu His Arg Ala Gly Ala Arg Leu
                        85                  90                  95

Asp Val Arg Asp Ala Trp Gly Arg Leu Pro Val Asp Leu Ala Glu Glu
            100                 105                 110

Leu Gly His Arg Asp Val Ala Arg Tyr Leu Arg Ala Ala Gly Gly
        115                 120                 125

Thr Arg Gly Ser Asn His Ala Arg Ile Asp Ala Ala Glu Gly Pro Ser
    130                 135                 140

Asp Ile Pro Asp
145

<210> SEQ ID NO 3
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (53)..(53)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (73)..(73)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (83)..(83)
<223> OTHER INFORMATION: a, c, t, g, unknown or other
<220> FEATURE:
<221> NAME/KEY: modified_base
<222> LOCATION: (89)..(89)
<223> OTHER INFORMATION: a, c, t, g, unknown or other
<220> FEATURE:
<221> NAME/KEY: modified_base
<222> LOCATION: (94)..(94)
<223> OTHER INFORMATION: a, c, t, g, unknown or other
<220> FEATURE:
<221> NAME/KEY: modified_base
<222> LOCATION: (119)..(119)
<223> OTHER INFORMATION: a, c, t, g, unknown or other
<220> FEATURE:
<221> NAME/KEY: modified_base
```

```
<222> LOCATION: (131)..(131)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (152)..(152)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (163)..(163)
<223> OTHER INFORMATION: a, c, t, g, unknown or other
<220> FEATURE:
<221> NAME/KEY: modified_base
<222> LOCATION: (179)..(180)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (215)..(215)
<223> OTHER INFORMATION: a, c, t, g, unknown or other
<220> FEATURE:
<221> NAME/KEY: modified_base
<222> LOCATION: (218)..(218)
<223> OTHER INFORMATION: a, c, t, g, unknown or other
<220> FEATURE:
<221> NAME/KEY: modified_base
<222> LOCATION: (220)..(220)
<223> OTHER INFORMATION: a, c, t, g, unknown or other
<220> FEATURE:
<221> NAME/KEY: modified_base
<222> LOCATION: (247)..(247)
<223> OTHER INFORMATION: a, c, t, g, unknown or other
<220> FEATURE:
<221> NAME/KEY: modified_base
<222> LOCATION: (269)..(269)
<223> OTHER INFORMATION: a, c, t, g, unknown or other
<220> FEATURE:
<221> NAME/KEY: modified_base
<222> LOCATION: (293)..(293)
<223> OTHER INFORMATION: a, c, t, g, unknown or other
<220> FEATURE:
<221> NAME/KEY: modified_base
<222> LOCATION: (338)..(338)
<223> OTHER INFORMATION: a, c, t, g, unknown or other
<220> FEATURE:
<221> NAME/KEY: modified_base
<222> LOCATION: (341)..(341)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other

<400> SEQUENCE: 3
ggnggnaagn tgtgggggaa agtttgggga tggaanacca anccctcctt tcnttaccaa      60
acnctggctc tgncgaggct ncntccgant ggtnccccg  ggggagaccc aacctgggnc     120
gacttcaggg ntgcnacatt cactaagtgc tnggagntaa tancacctcc tccgagcann    180
tcgctcacag cgtcccctta cctnganaga taccncgngn tccctccaga ggatttgagg     240
gacaggntcg gaggggctc  ttcccccanc accggaggaa gaaagaggag ggnctgactg    300
```

```
gtcaccagag ggtgggacgg accgcgtgcg ctcggcgnct ncggagaggg ggagaacaga    360
caacgggcgg cggggagcag catggatccg gcggcgggga gcagcatgga nccttcgact    420
gactgactgc ctcgc                                                     435
```

<210> SEQ ID NO 4
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (11)..(11)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (58)..(59)
<223> OTHER INFORMATION: a, c, t, g, unknown or other
<220> FEATURE:
<221> NAME/KEY: modified_base
<222> LOCATION: (110)..(110)
<223> OTHER INFORMATION: a, c, t, g, unknown or other
<220> FEATURE:
<221> NAME/KEY: modified_base
<222> LOCATION: (115)..(115)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (158)..(158)
<223> OTHER INFORMATION: a, c, t, g, unknown or other
<220> FEATURE:
<221> NAME/KEY: modified_base
<222> LOCATION: (185)..(185)
<223> OTHER INFORMATION: a, c, t, g, unknown or other
<220> FEATURE:
<221> NAME/KEY: modified_base
<222> LOCATION: (196)..(196)
<223> OTHER INFORMATION: a, c, t, g, unknown or other
<220> FEATURE:
<221> NAME/KEY: modified_base
<222> LOCATION: (199)..(199)
<223> OTHER INFORMATION: a, c, t, g, unknown or other
<220> FEATURE:
<221> NAME/KEY: modified_base
<222> LOCATION: (202)..(202)
<223> OTHER INFORMATION: a, c, t, g, unknown or other
<220> FEATURE:
<221> NAME/KEY: modified_base
<222> LOCATION: (224)..(224)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:

```
<221> NAME/KEY: modified_base
<222> LOCATION: (272)..(272)
<223> OTHER INFORMATION: a, c, t, g, unknown or other
<220> FEATURE:
<221> NAME/KEY: modified_base
<222> LOCATION: (291)..(291)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (335)..(335)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other

<400> SEQUENCE: 4
tcncttattg ntagganata ataacacctc caccgataac ttcacttaca acgtcccnnt      60
tcctggaaag atacacagcg ttccctccag aggatttgtg ggacagggtn ggagnggtct     120
cttccnccac caccggagga agaaagagga ggggctgnct gttcaccaga gggtgggacg     180
gaccncgtac gctcgncgnc tncggagagg gggagagcag tcancggncg ncggggagca     240
acatggaacc gncggcgggg agcagcatgg anccttcggc tgactggctg nccacgncca     300
cgncccgggg tcgggtagag gaggtgcggn cgctnctgga ggcggggnct ctgnccaacn     360 cgctaaaan                                                             369

<210> SEQ ID NO 5
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4)..(6)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (103)..(104)
<223> OTHER INFORMATION: a, c, t, g, unknown or other
<220> FEATURE:
<221> NAME/KEY: modified_base
<222> LOCATION: (200)..(200)
```

```
<223> OTHER INFORMATION: a, c, t, g, unknown or other
<220> FEATURE:
<221> NAME/KEY: modified_base
<222> LOCATION: (302)..(302)
<223> OTHER INFORMATION: a, c, t, g, unknown or other
<220> FEATURE:
<221> NAME/KEY: modified_base
<222> LOCATION: (346)..(346)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (380)..(380)
<223> OTHER INFORMATION: a, c, t, g, unknown or other
<220> FEATURE:
<221> NAME/KEY: modified_base
<222> LOCATION: (382)..(382)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (401)..(401)
<223> OTHER INFORMATION: a, c, t, g, unknown or other
<220> FEATURE:
<221> NAME/KEY: modified_base
<222> LOCATION: (403)..(403)
<223> OTHER INFORMATION: a, c, t, g, unknown or other

<400> SEQUENCE: 5
gacnnnctcc ggccggngtc gggtagagga ggtgcgggcg ctgctggagg cggggcgct      60 gcccaacgca ccgaatagtt acggtcggag gccgatccag gtnngggtag agggtctgca   120
gcgggagcag gggatggcgg gcgactctgg aggacgaagt ttgcagggga attggaatca   180
ggtagcgctt cgattctccn gaaaaagggg aggcttcctg gggagttttc agaagggggtt  240 tgtaatcaca gacctcctcc tggcgacgtc ctgggggctt gggaagccaa ggaagaggaa   300
tnaggagcca cgcgcgtaca gatctctcga atgctgagaa gatctnaagg ggggaacata   360
tttgtattag cntccaagtn tnctctntat canatacaaa ntnc                   404

<210> SEQ ID NO 6
<211> LENGTH: 401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other
<220> FEATURE:
<221> NAME/KEY: modified_base
<222> LOCATION: (37)..(37)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
```

```
<221> NAME/KEY: modified_base
<222> LOCATION: (134)..(135)
<223> OTHER INFORMATION: a, c, t, g, unknown or other
<220> FEATURE:
<221> NAME/KEY: modified_base
<222> LOCATION: (158)..(158)
<223> OTHER INFORMATION: a, c, t, g, unknown or other
<220> FEATURE:
<221> NAME/KEY: modified_base
<222> LOCATION: (164)..(164)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other
<220> FEATURE:
<221> NAME/KEY: modified_base
<222> LOCATION: (222)..(222)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (239)..(239)
<223> OTHER INFORMATION: a, c, t, g, unknown or other
<220> FEATURE:
<221> NAME/KEY: modified_base
<222> LOCATION: (244)..(244)
<223> OTHER INFORMATION: a, c, t, g, unknown or other
<220> FEATURE:
<221> NAME/KEY: modified_base
<222> LOCATION: (277)..(277)
<223> OTHER INFORMATION: a, c, t, g, unknown or other
<220> FEATURE:
<221> NAME/KEY: modified_base
<222> LOCATION: (280)..(281)
<223> OTHER INFORMATION: a, c, t, g, unknown or other
<220> FEATURE:
<221> NAME/KEY: modified_base
<222> LOCATION: (323)..(323)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (379)..(379)
<223> OTHER INFORMATION: a, c, t, g, unknown or other
<220> FEATURE:
<221> NAME/KEY: modified_base
<222> LOCATION: (388)..(388)
<223> OTHER INFORMATION: a, c, t, g, unknown or other

<400> SEQUENCE: 6
ctctnanccc gggtagaggg tctgcagcgg gagcagngga tggcgggcga ctctggagga      60
cgaagttggc aggggaattg gaatcaggta gcgcttcgan tctccggaaa aaggggaggc     120
ttcctgggga gttnncagaa ggggtttgta atcacagncc tccncctggc gacgccctgg    180
ggggttggga agccaaggaa gaggaatgag gagncacgcg cntacagntc tctcgaatnc    240
tganaagatc tgaaggggggg aacatatttg tattagnatn naagtatgct ctttatcaga    300
tacaaaattc acgaacgtgt ggnataaaaa gggagtctta aagaaatnta agatgtgctg    360
ggactactta gcctccaana cacagatncc tggatggagc t                        401

<210> SEQ ID NO 7
<211> LENGTH: 460
<212> TYPE: DNA
<213> ORGANISM: Artificial Sequence
<220> FEATURE:
<223> OTHER INFORMATION: Description of Artificial Sequence: Synthetic
```

```
        polynucleotide
<220> FEATURE:
<221> NAME/KEY: modified_base
<222> LOCATION: (5)..(6)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (61)..(61)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other

<400> SEQUENCE: 7
aaaannaaaa aaaatctccc aggcctaaca taattntcag gaaagaaatt tcagtagttg     60
natctcaggg gaaatacagg aagttagcct ggagtaaaag tcagtctgtc cctgcccctt    120
tgctanattg cccgtgcctc acagtgctct ctgcctgtga cgacagctcc ncagaagttc    180
ggaggatata atggaattca ttgtgtactg aagaatggat agagaactca agaaggaaat    240
tggaaactgg aagcaaatgt aggggtaatt agacacctgg ggcttgtgtg ggggtctgct    300
tggcggtgag ggggctctac acaagcttcc tttccgtcat gccgnccccc accctggctc    360
tgaccattct gttctctctg gcaggtcatg atgatgggca gcgcccgagt ggcggagctg    420
ctgctgctcc acggcgcgga gcccaactgc tccgacgccg                          460

<210> SEQ ID NO 8
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (91)..(91)
```

```
<223> OTHER INFORMATION: a, c, t, g, unknown or other
<220> FEATURE:
<221> NAME/KEY: modified_base
<222> LOCATION: (127)..(127)
<223> OTHER INFORMATION: a, c, t, g, unknown or other
<220> FEATURE:
<221> NAME/KEY: modified_base
<222> LOCATION: (161)..(162)
<223> OTHER INFORMATION: a, c, t, g, unknown or other
<220> FEATURE:
<221> NAME/KEY: modified_base
<222> LOCATION: (164)..(164)
<223> OTHER INFORMATION: a, c, t, g, unknown or other
<220> FEATURE:
<221> NAME/KEY: modified_base
<222> LOCATION: (167)..(167)
<223> OTHER INFORMATION: a, c, t, g, unknown or other
<220> FEATURE:
<221> NAME/KEY: modified_base
<222> LOCATION: (174)..(174)
<223> OTHER INFORMATION: a, c, t, g, unknown or other
<220> FEATURE:
<221> NAME/KEY: modified_base
<222> LOCATION: (232)..(232)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (262)..(262)
<223> OTHER INFORMATION: a, c, t, g, unknown or other
<220> FEATURE:
<221> NAME/KEY: modified_base
<222> LOCATION: (296)..(296)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (346)..(346)
<223> OTHER INFORMATION: a, c, t, g, unknown or other
<220> FEATURE:
<221> NAME/KEY: modified_base
<222> LOCATION: (352)..(352)
<223> OTHER INFORMATION: a, c, t, g, unknown or other
<220> FEATURE:
<221> NAME/KEY: modified_base
<222> LOCATION: (356)..(356)
<223> OTHER INFORMATION: a, c, t, g, unknown or other
<220> FEATURE:
<221> NAME/KEY: modified_base
<222> LOCATION: (358)..(358)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (376)..(376)
<223> OTHER INFORMATION: a, c, t, g, unknown or other
<220> FEATURE:
<221> NAME/KEY: modified_base
<222> LOCATION: (382)..(382)
<223> OTHER INFORMATION: a, c, t, g, unknown or other
<220> FEATURE:
<221> NAME/KEY: modified_base
<222> LOCATION: (385)..(385)
<223> OTHER INFORMATION: a, c, t, g, unknown or other

<400> SEQUENCE: 8
```

```
aanaaaaaag aaatngataa natagaggat gaacanatta aaatcaaaaa acanaacana      60
gacataataa aaaacgagaa tgttctagac ntaatcataa ttataaaggt caagactcat     120
tgatatnaag gaaattgaag ggaaatctta actagcacaa nngnatnaaa aaanaattcc     180
cacgacaccg ccactctcaa cgcatccgtg ctcgacactg cccgggaggt cntcctggac    240
acgctggtgg tnctccaccg gnccggggca cgtctggacg tgcgcgatgc ctgggnccgn    300
ctacccgtgg tacctgactg aggacctggg ccatcccgat ttcgcnggg t anctgngngn    360 ggctgngggg gccaanagag gncantaccc                                     390
```

<210> SEQ ID NO 9
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (94)..(94)
<223> OTHER INFORMATION: a, c, t, g, unknown or other
<220> FEATURE:
<221> NAME/KEY: modified_base
<222> LOCATION: (128)..(128)
<223> OTHER INFORMATION: a, c, t, g, unknown or other
<220> FEATURE:
<221> NAME/KEY: modified_base
<222> LOCATION: (136)..(136)
<223> OTHER INFORMATION: a, c, t, g, unknown or other
<220> FEATURE:
<221> NAME/KEY: modified_base
<222> LOCATION: (156)..(156)
<223> OTHER INFORMATION: a, c, t, g, unknown or other
<220> FEATURE:
<221> NAME/KEY: modified_base
<222> LOCATION: (207)..(208)
<223> OTHER INFORMATION: a, c, t, g, unknown or other
<220> FEATURE:
<221> NAME/KEY: modified_base
<222> LOCATION: (212)..(212)
<223> OTHER INFORMATION: a, c, t, g, unknown or other

<400> SEQUENCE: 9

```
cctgcnacga ccccgccact ctcacccgac ccgtgcacga cgctgtccgg gagggtttcc     60
tggacacgct ggtggtgctg caccgggccg gggncggtt ggacgtgcgc gatgcctggg    120
gccgcctncc cgtggnacct ggttgaggag ctgggncatc gcgatgtcgc acggtacctg   180
cgcgcggttg cgggggggcac cagaggnnag tnacc                              215
```

<210> SEQ ID NO 10
<211> LENGTH: 236
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (131)..(131)
<223> OTHER INFORMATION: a, c, t, g, unknown or other
<220> FEATURE:

```
<221> NAME/KEY: modified_base
<222> LOCATION: (145)..(145)
<223> OTHER INFORMATION: a, c, t, g, unknown or other
<220> FEATURE:
<221> NAME/KEY: modified_base
<222> LOCATION: (149)..(149)
<223> OTHER INFORMATION: a, c, t, g, unknown or other
<220> FEATURE:
<221> NAME/KEY: modified_base
<222> LOCATION: (155)..(155)
<223> OTHER INFORMATION: a, c, t, g, unknown or other
<220> FEATURE:
<221> NAME/KEY: modified_base
<222> LOCATION: (157)..(157)
<223> OTHER INFORMATION: a, c, t, g, unknown or other
<220> FEATURE:
<221> NAME/KEY: modified_base
<222> LOCATION: (176)..(177)
<223> OTHER INFORMATION: a, c, t, g, unknown or other
<220> FEATURE:
<221> NAME/KEY: modified_base
<222> LOCATION: (183)..(183)
<223> OTHER INFORMATION: a, c, t, g, unknown or other
<220> FEATURE:
<221> NAME/KEY: modified_base
<222> LOCATION: (198)..(198)
<223> OTHER INFORMATION: a, c, t, g, unknown or other
<220> FEATURE:
<221> NAME/KEY: modified_base
<222> LOCATION: (206)..(206)
<223> OTHER INFORMATION: a, c, t, g, unknown or other
<220> FEATURE:
<221> NAME/KEY: modified_base
<222> LOCATION: (209)..(209)
<223> OTHER INFORMATION: a, c, t, g, unknown or other
<220> FEATURE:
<221> NAME/KEY: modified_base
<222> LOCATION: (233)..(233)
<223> OTHER INFORMATION: a, c, t, g, unknown or other

<400> SEQUENCE: 10
nctctcacgg tggggaggcc aactgcgccg aacccgccac tctcacccga cccgcgcacg      60
acggtgcccg ggagggttc ctggacacgc tggtggtgct gcaccgggcc ggggcgcggc     120
tggacgttcg ngatgcctgg gggcntctnt ccgtngnacc tggctgaaga gctggnncat    180
cgngatgtcg cacggccnct gtgtgnggnt gcgggggca ccataggtca gtntcc         236

<210> SEQ ID NO 11
<211> LENGTH: 630
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (17)..(17)
<223> OTHER INFORMATION: a, c, t, g, unknown or other
<220> FEATURE:
<221> NAME/KEY: modified_base
<222> LOCATION: (34)..(34)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
```

-continued

```
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (70)..(70)
<223> OTHER INFORMATION: a, c, t, g, unknown or other
<220> FEATURE:
<221> NAME/KEY: modified_base
<222> LOCATION: (72)..(72)
<223> OTHER INFORMATION: a, c, t, g, unknown or other
<220> FEATURE:
<221> NAME/KEY: modified_base
<222> LOCATION: (85)..(85)
<223> OTHER INFORMATION: a, c, t, g, unknown or other
<220> FEATURE:
<221> NAME/KEY: modified_base
<222> LOCATION: (90)..(90)
<223> OTHER INFORMATION: a, c, t, g, unknown or other
<220> FEATURE:
<221> NAME/KEY: modified_base
<222> LOCATION: (100)..(100)
<223> OTHER INFORMATION: a, c, t, g, unknown or other
<220> FEATURE:
<221> NAME/KEY: modified_base
<222> LOCATION: (109)..(109)
<223> OTHER INFORMATION: a, c, t, g, unknown or other
<220> FEATURE:
<221> NAME/KEY: modified_base
<222> LOCATION: (113)..(113)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (131)..(131)
<223> OTHER INFORMATION: a, c, t, g, unknown or other
<220> FEATURE:
<221> NAME/KEY: modified_base
<222> LOCATION: (149)..(149)
<223> OTHER INFORMATION: a, c, t, g, unknown or other
<220> FEATURE:
<221> NAME/KEY: modified_base
<222> LOCATION: (166)..(166)
<223> OTHER INFORMATION: a, c, t, g, unknown or other
<220> FEATURE:
<221> NAME/KEY: modified_base
<222> LOCATION: (172)..(172)
<223> OTHER INFORMATION: a, c, t, g, unknown or other
<220> FEATURE:
<221> NAME/KEY: modified_base
<222> LOCATION: (186)..(186)
<223> OTHER INFORMATION: a, c, t, g, unknown or other
<220> FEATURE:
<221> NAME/KEY: modified_base
<222> LOCATION: (190)..(190)
<223> OTHER INFORMATION: a, c, t, g, unknown or other
<220> FEATURE:
<221> NAME/KEY: modified_base
<222> LOCATION: (193)..(193)
<223> OTHER INFORMATION: a, c, t, g, unknown or other
<220> FEATURE:
<221> NAME/KEY: modified_base
<222> LOCATION: (220)..(220)
<223> OTHER INFORMATION: a, c, t, g, unknown or other
<220> FEATURE:
<221> NAME/KEY: modified_base
<222> LOCATION: (225)..(225)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (256)..(256)
<223> OTHER INFORMATION: a, c, t, g, unknown or other
```

```
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (535)..(535)
<223> OTHER INFORMATION: a, c, t, g, unknown or other

<400> SEQUENCE: 11
naagtatgag cgaaacnaat tgtggtttga gaanaggnaa tcgtagggaa cttcgggatc      60
ccncngggan cnccagaacc tgagncgccn attggaaatn acaaactgnc tgnatcactc     120
cgnaccaggt ncaaaagata cctggggang cgggaaggga aagacnacat cnagaccgcc     180 ttcgcnccctn ggnattgtga gcagcctctg agactcattn atatnacact cgtntttctt    240
cttacaaccc tgcggnccgc gcggtcgcgc tttctctgcc ctccgccggg tggacctgga     300
gcgcttgagc ggtcggcgcg cctggagcag ccaggcggnc agtggactag ctgctggacc     360
agggaggtgt gggagagcgg tggcggcggg tacatgcacg tgaagccatt gcgagaactt     420
tatccataag tatttcaata ccggtaggga cggcaagaga ggagggcggg atgtgccaca     480
tatccataag tatttcaatg ccggtaggga cggcaagaga ggagggcggg atgtnccaca     540
catctttgac ctcaggtttc taacgcctgt tttctttctg ccctctgcag acaaccccga     600
ttgaaagaac cagagaggct ctgagaaacc                                       630

<210> SEQ ID NO 12
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (43)..(43)
<223> OTHER INFORMATION: a, c, t, g, unknown or other
<220> FEATURE:
<221> NAME/KEY: modified_base
<222> LOCATION: (80)..(80)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (111)..(111)
<223> OTHER INFORMATION: a, c, t, g, unknown or other
<220> FEATURE:
<221> NAME/KEY: modified_base
<222> LOCATION: (144)..(144)
<223> OTHER INFORMATION: a, c, t, g, unknown or other
<220> FEATURE:
<221> NAME/KEY: modified_base
<222> LOCATION: (151)..(151)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
```

```
<222> LOCATION: (207)..(207)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (355)..(355)
<223> OTHER INFORMATION: a, c, t, g, unknown or other
<220> FEATURE:
<221> NAME/KEY: modified_base
<222> LOCATION: (362)..(362)
<223> OTHER INFORMATION: a, c, t, g, unknown or other

<400> SEQUENCE: 12
ccccatcgcg ccttgggant gtgagcnacc attgagactc atnaatatag cactcgtttt      60
tcttcttgca accctgcggn ccgcgcggtc gcgctntctc tgccctccgc ngggtggacc     120
tggagcgctt gagcggtcgg cgcncctgga ncagccaggc gggcagtgga ctacctnctg     180
gaccagggag gtgtgggaga gcggtgncgg cgggtacatg cacgtgaagc cattgcgaga     240
acttcatctt tgacctcagg tttctaacgc ctgttttctt tctgccctct gcagacatcc     300
ccgattgaaa gaaccagaga ggctctgaga aacctccgga aacttagntc atcantcgcc     360 gnaaaa                                                               366

<210> SEQ ID NO 13
<211> LENGTH: 502
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (47)..(47)
<223> OTHER INFORMATION: a, c, t, g, unknown or other
<220> FEATURE:
<221> NAME/KEY: modified_base
<222> LOCATION: (68)..(68)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (170)..(170)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (380)..(380)
<223> OTHER INFORMATION: a, c, t, g, unknown or other
<220> FEATURE:
<221> NAME/KEY: modified_base
<222> LOCATION: (383)..(383)
<223> OTHER INFORMATION: a, c, t, g, unknown or other
<220> FEATURE:
<221> NAME/KEY: modified_base
<222> LOCATION: (386)..(386)
<223> OTHER INFORMATION: a, c, t, g, unknown or other
```

<220> FEATURE:
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: modified_base
<222> LOCATION: (467)..(467)
<223> OTHER INFORMATION: a, c, t, g, unknown or other
<220> FEATURE:
<221> NAME/KEY: modified_base
<222> LOCATION: (479)..(479)
<223> OTHER INFORMATION: a, c, t, g, unknown or other
<220> FEATURE:
<221> NAME/KEY: modified_base
<222> LOCATION: (490)..(490)
<223> OTHER INFORMATION: a, c, t, g, unknown or other
<220> FEATURE:
<221> NAME/KEY: modified_base
<222> LOCATION: (495)..(496)
<223> OTHER INFORMATION: a, c, t, g, unknown or other

<400> SEQUENCE: 13
agaaattaga tcatcagtca ccgatggtcc tacagggnca caactgnccc cgccacaacc      60
caccccgntt tcgtagtttt catttagaaa atagagcttt taaaaatgtc ctgccttta     120 acgtagatat atgccttccc ccactaccgn aaatgtccat ttatatcatn ttttatatat    180
tcttataaaa atgtaaaaaa gaaaacacc gcttctgcct tttcactgtg ttggagtttt     240
ctggagtgag cactcacgcc ctaagcgcac attcatgtgg gcatttcttg cgagcctcgc    300
agnctccgga agctgtcgac ctcgaggggg ggnccggtac ccaattcgcc ctatagtgag    360
tcgtattaca attcactggn cgncgntttt acaacgtcgg tggactggga aaaccccggn    420
gttacccaac tttaatcgnc ttggaggaca tcccccttt cgccagntgg ggttatagng    480
aagagggccn caccnntcgc cc                                             502

<210> SEQ ID NO 14
<211> LENGTH: 503
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base -continued

```
<222> LOCATION: (45)..(45)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (68)..(68)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other
<220> FEATURE:
<221> NAME/KEY: modified_base
<222> LOCATION: (122)..(122)
<223> OTHER INFORMATION: a, c, t, g, unknown or other
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (176)..(176)
<223> OTHER INFORMATION: a, c, t, g, unknown or other
<220> FEATURE:
<221> NAME/KEY: modified_base
<222> LOCATION: (179)..(179)
<223> OTHER INFORMATION: a, c, t, g, unknown or other
<220> FEATURE:
<221> NAME/KEY: modified_base
<222> LOCATION: (192)..(192)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other
<220> FEATURE:
<221> NAME/KEY: modified_base
<222> LOCATION: (248)..(248)
<223> OTHER INFORMATION: a, c, t, g, unknown or other
<220> FEATURE:
<221> NAME/KEY: modified_base
<222> LOCATION: (307)..(307)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (320)..(320)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (349)..(349)
<223> OTHER INFORMATION: a, c, t, g, unknown or other
<220> FEATURE:
```

```
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (413)..(413)
<223> OTHER INFORMATION: a, c, t, g, unknown or other
<220> FEATURE:
<221> NAME/KEY: modified_base
<222> LOCATION: (421)..(421)
<223> OTHER INFORMATION: a, c, t, g, unknown or other
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: modified_base
<222> LOCATION: (449)..(449)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (471)..(471)
<223> OTHER INFORMATION: a, c, t, g, unknown or other
<220> FEATURE:
<221> NAME/KEY: modified_base
<222> LOCATION: (473)..(473)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (488)..(488)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other

<400> SEQUENCE: 14
cancnatntn cggcatttct ngngagcctc gtagtctccg gatgntgtcg acctcgaggg      60
ggggnccngt acccaattcg ncctatngtg agtcgtntta caattcactg gccgccgttt    120
tnacaacgtc gntgnactgg gaaaaccctg gtgttaccca acttnaatcg ccttgnagna    180 catcccccctt tncgccagct ggtgtaatag cgangaggcc cgcaccgatc gcccttccca    240
acagttgngc agcctgaatg gcgaatggaa attgtaagcg ttaatatttt gttaaaattc    300
gcgttanatc ntcggttaan tcagctcatn ttttatccaa taggccgana tcggcanaat    360
ccccaataaa tcaanagaat agaccgagat agggttgagt gtcgttccag ttngggaaca    420
ngagtccact attaaaganc gtagnctcna acgtcanagg gcgaaaaacc ntntttcagn    480
ggattggncc actacgcnta ncc                                            503

<210> SEQ ID NO 15
<211> LENGTH: 515
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (23)..(23)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (68)..(68)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (97)..(97)
<223> OTHER INFORMATION: a, c, t, g, unknown or other
<220> FEATURE:
<221> NAME/KEY: modified_base
<222> LOCATION: (122)..(122)
<223> OTHER INFORMATION: a, c, t, g, unknown or other
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (176)..(176)
<223> OTHER INFORMATION: a, c, t, g, unknown or other
<220> FEATURE:
<221> NAME/KEY: modified_base
<222> LOCATION: (179)..(179)
<223> OTHER INFORMATION: a, c, t, g, unknown or other
<220> FEATURE:
<221> NAME/KEY: modified_base
```

-continued

```
<222> LOCATION: (192)..(192)
<223> OTHER INFORMATION: a, c, t, g, unknown or other
<220> FEATURE:
<221> NAME/KEY: modified_base
<222> LOCATION: (214)..(214)
<223> OTHER INFORMATION: a, c, t, g, unknown or other
<220> FEATURE:
<221> NAME/KEY: modified_base
<222> LOCATION: (248)..(248)
<223> OTHER INFORMATION: a, c, t, g, unknown or other
<220> FEATURE:
<221> NAME/KEY: modified_base
<222> LOCATION: (307)..(307)
<223> OTHER INFORMATION: a, c, t, g, unknown or other
<220> FEATURE:
<221> NAME/KEY: modified_base
<222> LOCATION: (311)..(311)
<223> OTHER INFORMATION: a, c, t, g, unknown or other
<220> FEATURE:
<221> NAME/KEY: modified_base
<222> LOCATION: (320)..(320)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (349)..(349)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (413)..(413)
<223> OTHER INFORMATION: a, c, t, g, unknown or other
<220> FEATURE:
<221> NAME/KEY: modified_base
<222> LOCATION: (421)..(421)
<223> OTHER INFORMATION: a, c, t, g, unknown or other
<220> FEATURE:
<221> NAME/KEY: modified_base
<222> LOCATION: (439)..(439)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: modified_base
<222> LOCATION: (449)..(449)
<223> OTHER INFORMATION: a, c, t, g, unknown or other
<220> FEATURE:
<221> NAME/KEY: modified_base
<222> LOCATION: (457)..(457)
<223> OTHER INFORMATION: a, c, t, g, unknown or other
<220> FEATURE:
<221> NAME/KEY: modified_base
<222> LOCATION: (471)..(471)
<223> OTHER INFORMATION: a, c, t, g, unknown or other
<220> FEATURE:
<221> NAME/KEY: modified_base
<222> LOCATION: (473)..(473)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (488)..(488)
<223> OTHER INFORMATION: a, c, t, g, unknown or other
<220> FEATURE:
```

```
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other

<400> SEQUENCE: 15
cancnatntn cggcatttct ngngagcctc gtagtctccg gatgntgtcg acctcgaggg      60
ggggnccngt acccaattcg ncctatngtg agtcgtntta caattcactg gccgccgttt     120
tnacaacgtc gntgnactgg gaaaaccctg gtgttaccca acttnaatcg ccttgnagna     180
catccccctt tncgccagct ggtgtaatag cgangaggcc cgcaccgatc gcccttccca     240
acagttgngc agcctgaatg gcgaatggaa attgtaagcg ttaatatttt gttaaaattc     300
gcgttanatc ntcggttaan tcagctcatn ttttatccaa taggccgana tcggcanaat     360
ccccaataaa tcaanagaat agaccgagat agggttgagt gtcgttccag ttngggaaca     420
ngagtccact attaaaganc gtagnctcna acgtcanagg gcgaaaaacc ntntttcagn     480
ggattggncc actacgcnta nccatcaccc tattc                                515
```